United States Patent [19]

Genna et al.

[11] Patent Number: 4,859,852
[45] Date of Patent: Aug. 22, 1989

[54] COLLIMATOR SYSTEM WITH IMPROVED IMAGING SENSITIVITY

[75] Inventors: Sebastian Genna, Belmont; Andrew P. Smith, Medford, both of Mass.

[73] Assignee: Digital Scintigraphics, Inc., Cambridge, Mass.

[21] Appl. No.: 40,941

[22] Filed: Apr. 21, 1987

Related U.S. Application Data

[63] Continuation-in-part of Ser. No. 876,811, Jun. 20, 1986, Pat. No. 4,782,233.

[51] Int. Cl.⁴ ............................................. G01T 1/164
[52] U.S. Cl. ................................. 250/363.1; 250/505.1
[58] Field of Search ............... 250/363 SH, 369, 505.1

[56] References Cited

U.S. PATENT DOCUMENTS

| 4,389,569 | 6/1983 | Hattori et al. | 250/363 SH |
|---|---|---|---|
| 4,584,478 | 4/1986 | Genna et al. | 250/363 SH |
| 4,659,935 | 4/1987 | Hawman | 250/363 SH |
| 4,748,328 | 5/1988 | Chang et al. | 250/363 SH |
| 4,774,410 | 9/1988 | Hsieh | 250/363 SH |

FOREIGN PATENT DOCUMENTS

| 1159179 | 7/1986 | Japan | 250/363 SH |
|---|---|---|---|
| 1159180 | 7/1986 | Japan | 250/363 SH |

Primary Examiner—Carolyn E. Fields
Assistant Examiner—John A. Miller
Attorney, Agent, or Firm—Joseph S. Iandiorio; Douglas E. Denninger

[57] ABSTRACT

A collimator system rotatable about an axis of rotation for use in a radionuclide emission tomography camera for imaging a region of an object, including a collimator having a number of collimator elements for restricting and collimating the radionuclide emissions. The collimator elements are disposed with their axes intersecting at least one line, parallel to the axis of rotation, at at least two different angles. The collimator elements establish a selected variation in imaging sensitivity across the imaging region.

31 Claims, 23 Drawing Sheets

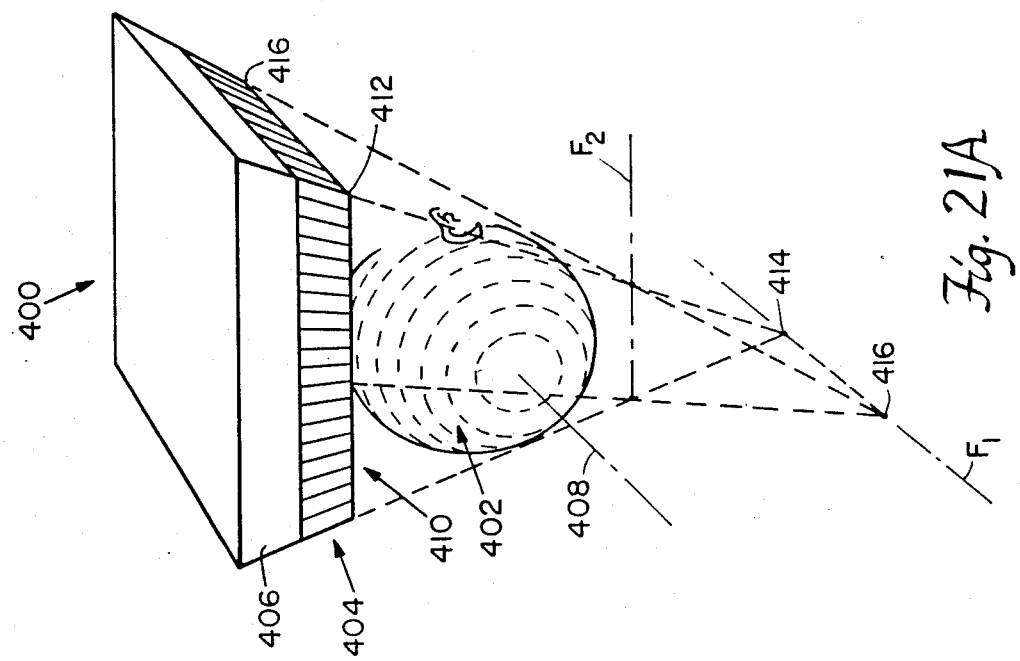
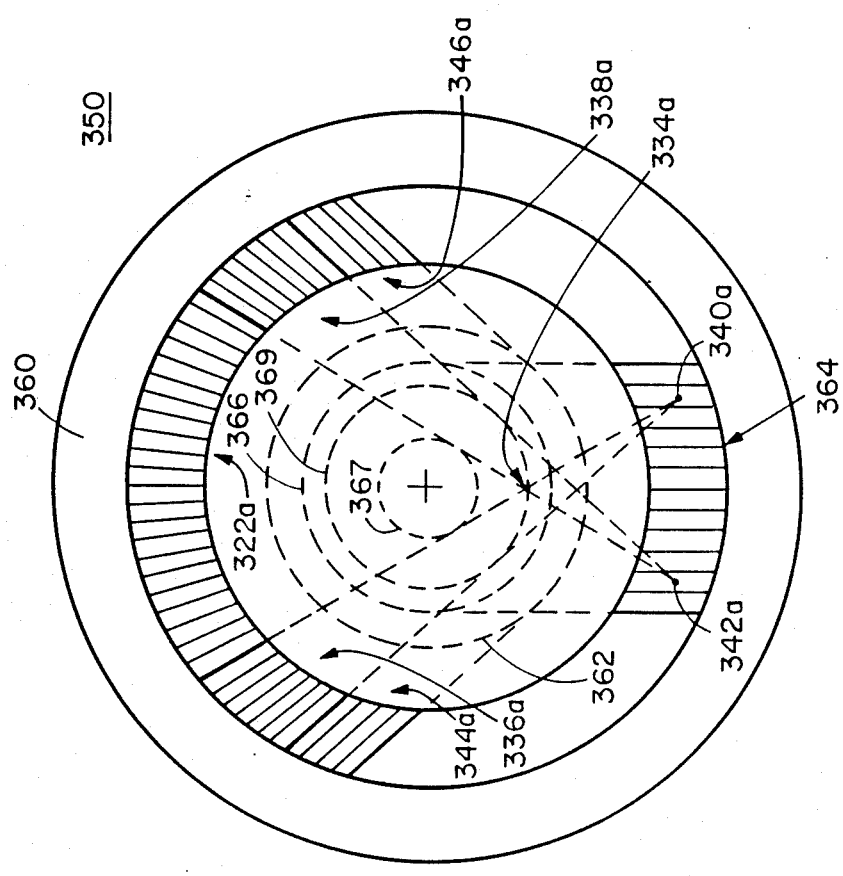
Fig. 21A
Fig. 19

COLLIMATOR SYSTEM WITH IMPROVED IMAGING SENSITIVITY

RELATED APPLICATIONS

This application is a continuation-in-part of U.S. patent application Ser. No. 876,811, now U.S. Pat. No. 4,782,233 Genna et al., Multifield Collimator System and Method and Radionuclide Emission Tomography Camera Using Same, filed June 20, 1986.

FIELD OF INVENTION

This invention relates to the imaging of objects by radionuclide emission tomography utilizing a rotating collimator system and more particularly to such a collimation system for establishing a selected variation in sensitivity across the object being imaged.

BACKGROUND OF INVENTION

Conventional radionuclide emission tomography cameras construct three-dimensional images of an object's radionuclide distribution from a sequence of two-dimensional images collected through one or more collimators from a large number of viewing angles, that is, viewing positions, around the object being imaged. The very nature of the image reconstruction process, that is, the underlying mathematical theory and associated computer reconstruction algorithms, is such that in a preferred construction a tomographic field of view in the camera system encompasses the entire object being imaged. A tomographic field of view is the enclosed region of a field defined by the intersections of one or more collimator fields of view in a plane transverse to the axis of rotation as the collimators rotate about the object through $2\pi$ radians. Failure to include the entire imaged object in a tomographic field of view results in insufficient information to uniquely reconstruct its three-dimensional radionuclide distribution.

When a rotating planar radionuclide camera is employed to collect the images for reconstruction, a single continuous parallel hole or converging hole collimator, having a number of channels (holes) and a field of view encompassing the object, is typically used to restrict emissions received by the camera detector from the object to those gamma rays following parallel or diverging projections toward the detector. In the case of stationary annular camera detector with rotating collimator, disclosed for example by the patents of Hattori et al., U.S. Pat. Nos. 4,389,569, and Genna et al., 4,584,478, a rotating annular collimator system is segmented into a multiplicity of either parallel hole or converging hole collimator segments; however, each of these collimator segments still has, in a plane normal to the axis of rotation, a tomographic field of view as large as, or larger, than the imaged object, and provides only one such field of view.

A shortcoming of both of these systems is that the imaged object's radionuclide distribution is sampled in a plane normal to the axis of rotation either with uniform efficiency in the case of the parallel hole collimator or, in the case of the annular camera with rotating converging hole collimator, the center of the tomographic field of view is sampled with a lower efficiency than the periphery. Experimental studies of the effect of uniform sampling (Pang, S. C. and Genna, S., "Noise Propagation in 3-D Fourier Convolution Reconstruction" in *Image Processing for 2-D and 3-D Reconstruction from Projections*, Optical Society of America, PD-11, 1975) using a uniformly emitting water phantom have shown a substantial increase in the variance per pixel or decrease in the signal-to-noise ratio of the reconstructed data near the central portion of the imaged phantom. In clinical applications, however, the central regions of an imaged human body part are typically those in which enhanced imaging ability is desired, i.e., less variance in the measured data.

Present two-dimensional rotating collimator systems with two or more rows of channels sample a radionuclide distribution with uniform efficiency along lines parallel to the axis of rotation. The shortcomings described above apply also to sampling in the second dimension parallel to the axis of rotation.

SUMMARY OF INVENTION

It is therefore a primary object of this invention to improve imaging sensitivity by varying the imaging sensitivity along lines parallel to the axis of rotation of radionuclide emission tomography cameras in portions of an imaged object exhibiting the greatest clinical interest.

It is a further object of this invention to enhance camera efficiency in one or more portions of the imaged object along lines parallel to the axis of rotation by constructing a collimator to provide greater imaging sensitivity in those portions.

Yet another object of this invention is to provide an improved two-dimensional collimator which provides both greater imaging sensitivity and greater inherent resolution in both dimensions in selected portions of the object.

It is a further object of this invention to provide such a collimator which can be smaller in size than conventional two-dimensional collimators yet provide higher sensitivities.

It is a further object of this invention to provide such a collimator which enables more efficient use of an associated detector.

This invention results from the realization that truly effective collimation of radionuclide emissions from a region of an object to enhance imaging sensitivity as desired can be achieved by imaging a region with a collimator having a number of collimator elements with their axes disposed at two or more different angles relative to one or more lines, intersected by the collimator element axes, which are parallel to the axis of rotation, the collimator elements establishing the desired enhancement of imaging sensitivity across the imaging region.

This invention features a collimator system rotatable about its axis of rotation for use in a radionuclide emission tomography camera for imaging a region. There is a collimator having a plurality of collimator elements for restricting and collimating the region of radionuclide emissions within a field of view of the collimator. The collimator elements are disposed with their axes intersecting at least one line, parallel to the axis of rotation and within the collimator field of view, at at least two different angles. The collimator elements establish a selected variation in imaging sensitivity across the imaging region.

In one embodiment, each collimator element axis is disposed at a different angle. The collimator elements may converge or diverge in at least one plane parallel to the axis of rotation.

This invention also features a collimator system having a collimator with a plurality of collimator elements being disposed with their axes in at least two sets. At least one collimator element axis in one set intersects a line, parallel to the axis of rotation and within the collimator field of view, at a different angle from at least one collimator element least two different imaging sensitivities across the imaging region.

In one embodiment, in at least one set, the collimator elements within that set have the same collimator angle. In at least one set the collimator elements within that set may have collimator element angles which differ from each other.

In another embodiment, the collimator includes a collimator structure having each set of the collimator elements arranged in a different section, each section having a field of view proximate the field of view of the other section. Each section establishes one of the different imaging sensitivities within its field of view. The fields of view in this embodiment are non-overlapping, and at least one of the sections is divided into two parts, one part being disposed on each side of the other section. The collimator elements may be continuous throughout the collimator structure and are contiguous to each other. The fields of view of the sections may encompass the entire object, and one or more of the sections may exhibit uniform or non-uniform imaging sensitivity throughout the section. At least one of the sections may be selected from the group consisting of a parallel-type collimator, a converging type collimator, and a diverging type collimator. The collimator structure may be an angular rotating collimator or a planar collimator.

In yet another embodiment, each set of collimator elements is a separate collimator segment, the fields of view of the segments establishing the different imaging sensitivities. The fields of view of the collimators overlap at least in part and enhance imaging sensitivity in the portion of overlap. The field of view of one of the collimators may completely overlap that of the other collimator, so that the other, overlapped collimator enhances imaging sensitivity throughout its field of view. At least one of the sets of collimator elements may have at least one collimator element axis substantially parallel to the axis of rotation.

This invention further features a radionuclide emission tomography camera for imaging a region of an object, including a collimator having a plurality of collimator elements disposed with their axes intersecting at least one line, parallel to the axis of rotation, at at least two different angles. The collimator elements establish a selected variation in imaging sensitivity across the imaging region. The camera further includes the means responsive to the collimator for detecting radionuclide emissions from the region to collect at least one collimated image through each collimator element, and means for combining the collimated images to produce a final image of the region exhibiting the different imaging sensitivities.

DISCLOSURE OF PREFERRED EMBODIMENTS

Other objects, features and advantages will occur from the following description of a preferred embodiment and the accompanying drawings, in which:

FIG. 19 is a schematic diagram of a compound collimator combined with a separate collimator segment having an overlapping tomographic field of view;

FIG. 21A is a schematic axonometric view of a collimator system according to this invention having a number of collimator elements with their axes intersecting lines, parallel to the axis of rotation, at a number of different angles;

This invention may be accomplished by a collimation system for use with a radionuclide emission tomography camera, having a collimator with a number of collimator elements which restrict and collimate radionuclide emissions. The collimator elements are disposed with their axes intersecting one or more lines parallel to the axis of rotation and within the collimator field of view. Each line is intersected at two or more angles by a number of collimator element axes. The angling of the collimator element axes enables the collimator elements to establish a selected variation in imaging sensitivity across an imaging region within the collimator field of view.

A collimator system according to this invention may restrict and collimate the radionuclide emissions utilizing collimator elements disposed in at least two sets. In one construction, the system is a compound collimator having collimator elements arranged in at least two sections, each section having a field of view adjacent to the field of view of the other section. Compound collimators having multiple collimator element axis angles in a plane transverse to the axis of rotation are shown in FIGS. 10-20.

In another construction, the collimator system is a multifield collimator having at least two collimator segments with overlapping fields of view which establish different imaging sensitivities along lines parallel to the axis of rotation. Multifield collimators having a number of collimator element axis angles in a plane transverse to the axis of rotation are shown in FIGS. 5-9A.

Figure 1:
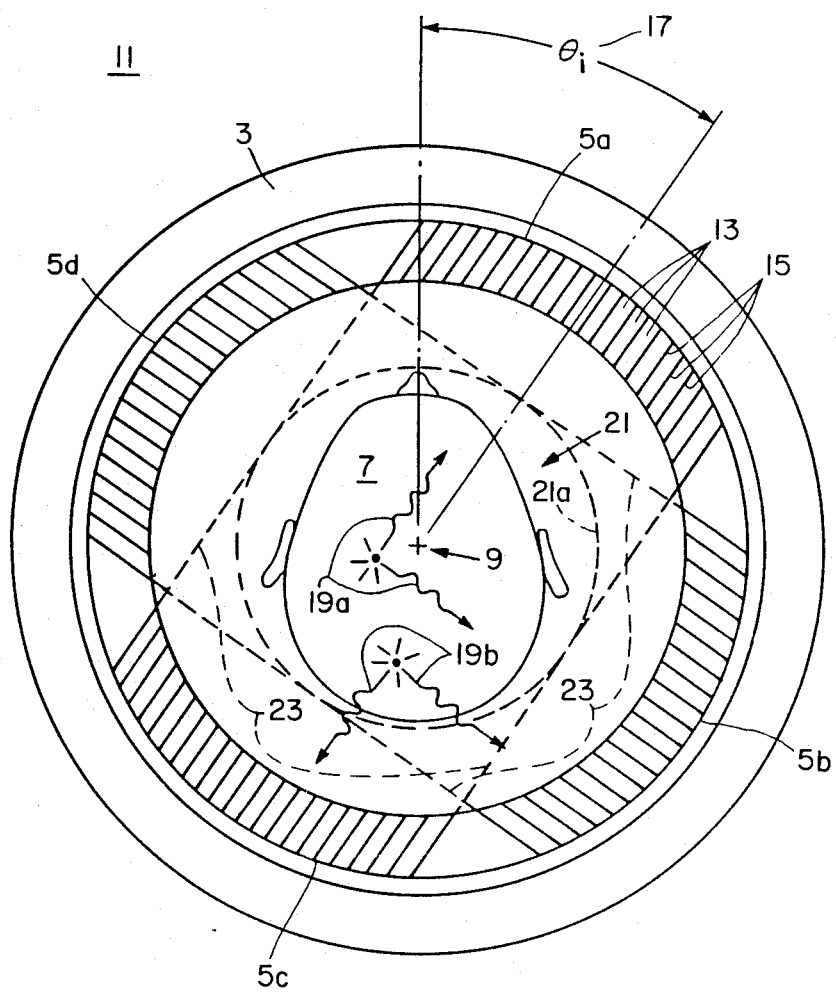
FIG. 1 is a schematic diagram of a conventional annular collimator system employing several parallel type collimator segments that illustrates the difference between the collimator field of view and the tomographic field of view, that is, the view within the boundary defined by the rotating collimator field of view.

There is shown in FIG. 1 a conventional collimator system consisting of several parallel type collimator segments 5a, 5b, 5c, 5d for use in annular radionuclide emission tomography camera 11. Each collimator segment has the same size field of view 23 as established by a multiplicity of equal hole size channels 13 separated by lead septa 15, and these fields of view are at least as wide as the breadth of the object 7 that is being imaged by position detector 3. The collimator segments 5a-5d rotate incrementally by angle 17 about axis of rotation 9, perpendicular to the page in FIG. 1, in order to generate a sequence of images surrounding the entire imaged object 7. This sequence of images is used to reconstruct the three-dimensional radionuclide distribution contained within imaged object 7. The mathematical theory and computer algorithms underlying the reconstruction process are such that the collimator segment field of view 23 must encompass the entire imaged object 7 at each of the angles 17 of view $\theta_i$.

There is also shown in FIG. 1 the tomographic field of view 21 having a boundary 21a which is defined as the intersection of the individual collimator segment fields of view 23 as the collimator segments 5a-5d rotate continuously through 360 degrees about axis of rotation 9. Only radionuclide distributions contained within the tomographic field of view 21 can be uniquely reconstructed into three-dimensional images; boundary 21a of tomographic field of view 21 represents the outermost radial position in relation to axis of rotation 9 of imaging of which camera 11 is capable. In the system of FIG. 1 four collimator segments 5a, 5b, 5c, 5d exhibit the same size segment field of view 23 and the same tomographic field of view 21. The sampling efficiency of this system is therefore the same throughout the tomographic field of view. In practice, however, radionuclide emission signals (gamma rays) 19a from the central portions of imaged object 7 typically travel through a greater thickness of the imaged object than emission signals 19b from the peripheral regions of the imaged object. Emissions produce gamma radiation 19a, 19b isotropically in the region surrounding the emission event, but such isotropy is not illustrated in FIG. 1 for clarity. Signals 19a from the central portion of imaged object 7 are thus detected by detector 3 with a lower signal-to-noise ratio than those from the peripheral regions of imaged object 7.

Figure 2:
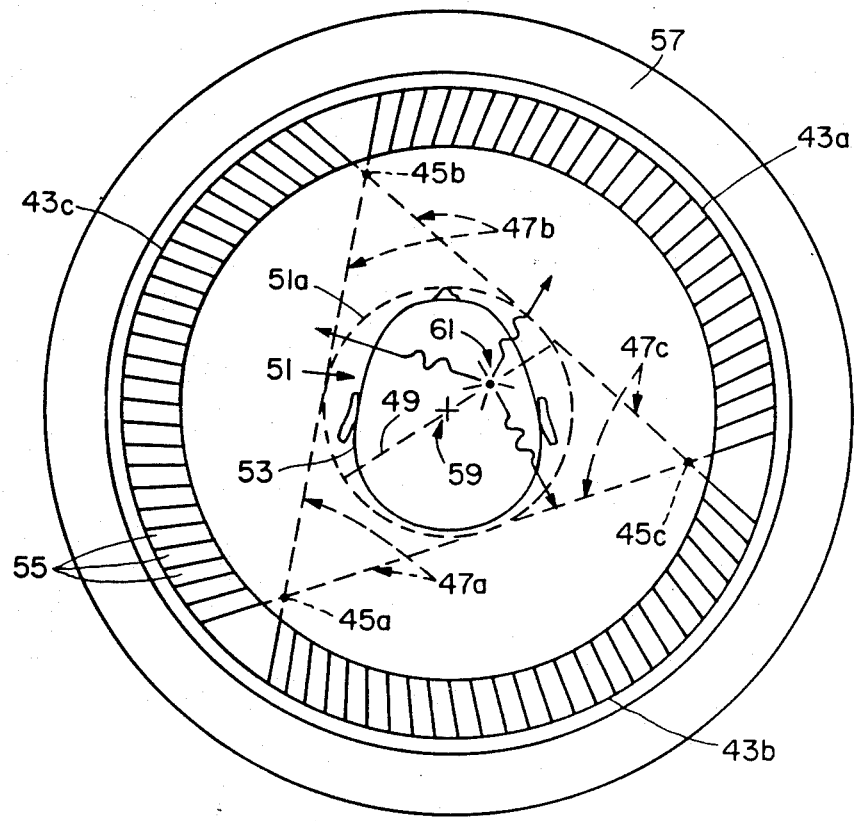
FIG. 2 is a schematic diagram of a conventional annular collimator system employing several converging type collimator segments.

FIG. 2 shows a conventional annular collimator system 41 employing three collimator segments 43a, 43b, 43c of the converging type. For each collimator segment 43, the equal size collimator channels 55 converge, respectively, to a point 45a, 45b, 45c located beyond axis of rotation 59. The individual collimator segment fields of view 47a, 47b, 47c, all the same size in this case, produce a single overlapped tomographic field of view 51 having boundary 51a as each segment rotates through 360 degrees about axis 59 that encompasses the entire imaged object 53. The system 41 of FIG. 2 illustrates a conventional implementation used in an annular radionuclide tomography camera. If the converging collimators have uniform hole dimensions, the composite response of position detector 57 to an emission event 61 positioned along a diameter 49 of the tomographic field of view 51 increases with increasing radial displacement of event 61 from axis of rotation 59 as the collimator segments rotate 360° about axis 59. Thus, in the absence of attenuation, an emission event 61 whose location along diameter 49 is further from axis 59 will result in a larger composite signal (that is, the sum of signals produced by the complete set of collimator segments 43a, 43b, 43c) than an event whose location is closer to axis 59. Although FIG. 2 illustrates a conventional collimator system employing three collimator segments 43, any number of such segments may be employed.

Figure 3:
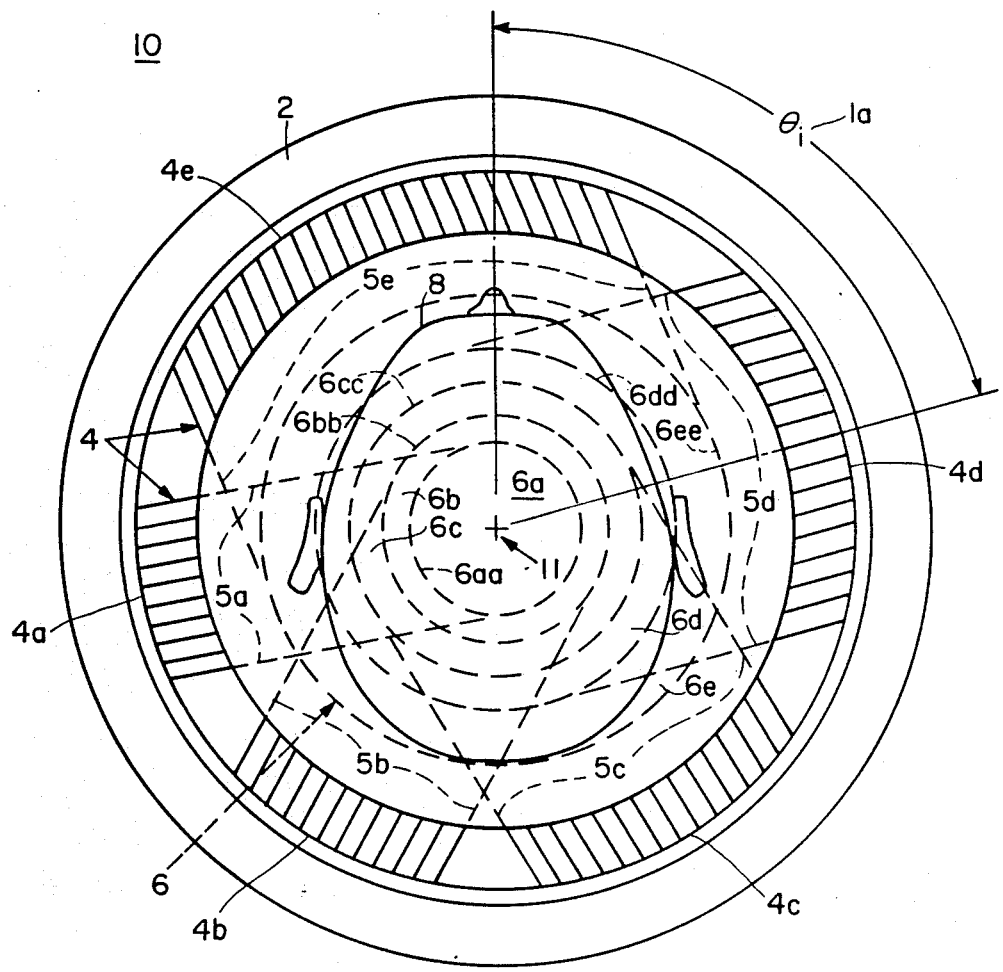
FIG. 3 is a schematic diagram of a novel multifield annular collimator system employing several parallel type collimator segments with different fields of view in which one of the collimator segments defines a tomographic field of view having a boundary which encompasses the object.

There is shown in FIG. 3 a collimator system 10 for a novel annular radionuclide emission tomography camera. The camera comprises a scintillation position detector 2 and collimator segments 4. Scintillation detector 2 consists of means for detecting the positions of scintillations produced by gamma rays emitted by radionuclides contained within the imaged object 8. Collimator segments 4a, 4b, 4c, 4d and 4e accept emission signals only from sources within their respective collimator fields of view 5a, 5b, 5c, 5d and 5e. An image from each collimator segment centered at one of a umber of view positions such as position 1, shown at the angle 1a of view $\theta_i$, is combined with other images obtained at that position from the remaining collimator segments when they are rotated to that angle of view to develop a composite image of object 8 for each view position. The imaged object 8 in FIG. 3 is shown as a human head whose radionuclide distribution is being imaged for three-dimensional reconstruction by the radionuclide emission camera system of which collimator system 10 is a part. The entire disclosure of the following U.S. Patents are incorporated herein by reference, including their disclosures of radionuclide emission camera systems: Genna et al., U.S. Pat. Nos. 4,095,107; Genna et al., 4,228,515; Genna et al., 4,584,478; and Pang et al., 4,593,198.

Tomographic fields-of-view 6a, 6b, 6c, 6d, 6e having boundaries 6aa, 6bb, 6cc, 6dd, 6ee, respectively, are formed as a result of multiple viewing by collimator segments 4a, 4b, 4c, 4d, 4e, during tomographic imaging as the collimator is rotated through $2\pi$ radians. Tomographic fields of view 6a–6e overlap and in this construction are concentric since segments 4a–4e share the same axis of rotation 11. Gamma ray emissions occurring within the overlapping tomographic fields of view 6a, 6b, 6c, 6d of collimator segments 4 as defined earlier are imaged with enhanced efficiency or sensitivity. Thus, the central tomographic field of view 6a in FIG. 3 in which all five tomographic fields of view 6 overlap is imaged with greater efficiency than any of the other overlapping central tomographic fields of view. The next central tomographic field of view, 6b, for example, is fully imaged only by four of the five collimator segments 4, and therefore the imaging efficiency or sensitivity in field of view 6b is less than that of view 6a.

Although five collimator segments 4 with five different tomographic fields of view 6 are shown in FIG. 3, this is not an inherent limitation. Any number of collimator segments greater than one may be used, and the tomographic fields of view may be of any desired spatial extent relative to the imaged object 8, as long as at least one boundary of the tomographic fields of view encompasses the imaged object. To uniquely reconstruct the three-dimensional radionuclide distribution in an object, at least one tomographic field of view boundary must encompass the entire object as the collimator system is rotated through $2\pi$ radians. However, it is known in the art to perform incomplete sampling which does not uniquely reconstruct the image but still provides useful information. Partial rotation of a collimator system according to this invention produces at least two incomplete tomographic fields of view each having an incomplete outer boundary which is not a closed curve. Useful information may still be obtained from the incomplete tomographic fields of view, depending on the accuracy desired. Similarly, incomplete enclosure by the outermost boundary of the entire object, e.g., encompassing as a region all or a portion of the brain itself but not the skull of a patient, may also provide useful information and is also within the scope of this invention. The phrase "encompass the region to be imaged" hereinafter includes encompassing only that portion of the object which the observer wishes to image, whether or not the object in its entirety is encompassed.

Further, the collimator segments 4 may be of any type, parallel, the type shown in FIG. 3, converging or diverging. A parallel type collimator segment is one whose axis of convergence for imaged emission signals lies along an axis infinitely far from the collimator segment. A converging type collimator segment is one whose axis of convergence lies along an axis positioned at some point in the half-space containing the collimator segment and the emission source, but not at the point at infinity. And, a diverging collimator segment is one whose axis of convergence lies at some point outside the half-space containing the emission source and the collimator segment, but not at the point at infinity. The three types of collimator segments, parallel, converging, and diverging, are well-known in the art, and are frequently described as collimator segments with "infinite," "positive" and "negative" focal lengths, respectively. Hereinafter these different terminologies may be used interchangeably or in mixed form in order to describe various types of collimator segments.

Figure 4:
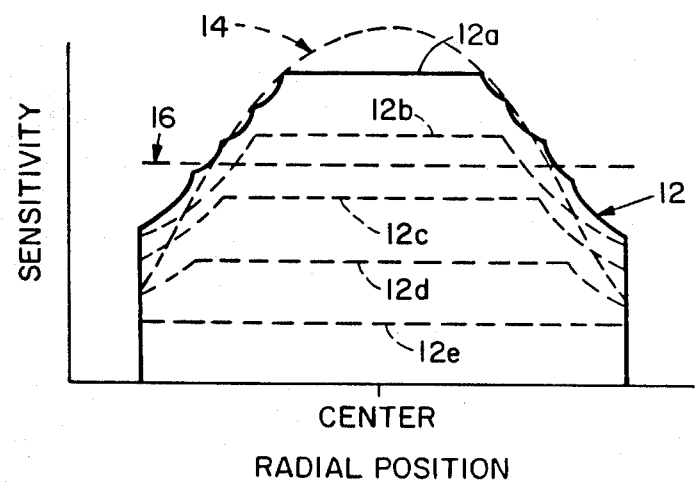
FIG. 4 is a graph of the relative sensitivity distribution (relative sampling efficiency as a function of radial position in the tomographic field of view) for a multifield collimator system employing parallel-element uniform-sensitivity collimator segments.

FIG. 4 illustrates the relative sensitivity variation as a function of radial position in the tomographic field-of-view for several different types of collimator structures. The sensitivity distribution is a composite of collimated images centered at the same position, e.g., position 1, FIG. 3. One or more collimators that image the entire field of view uniformly exhibit the response shown in dashed curve 16, FIG. 4. Because different emission source points in the typical imaged object result in varying signal propagation path lengths through the imaged object, a uniform response curve such as curve 16 leads to a signal-to-noise ratio in the reconstructed image that decreases in central regions where the path length for emission signals is longer. This feature of typical radionuclide emission tomography cameras may be mitigated by varying the imaging sensitivity as a function of radial position in such a manner that it is increased in regions where the emission signal path length through the imaged object is longer.

An idealized non-uniform sensitivity curve 14 is shown in FIG. 4 in which maximum sensitivity occurs at the center of the imaged object. In order to achieve a continuously varying sensitivity curve such as curve 14, however, an infinite number of infinitely small collimator segments is required. In a practical collimation system, of course, only a finite number of collimator segments can be used, with the result that only an approximation to idealized curve 14 can be obtained. Continuous curve 12 in FIG. 4 illustrates a typical approximation to curve 14 achievable with a finite number of collimator segments as, for example, in the system of FIG. 3. Each collimator segment exhibits a uniform sampling efficiency, and the cumulative effect of imaging certain portions of the imaged object with overlapping tomographic fields of view from the several collimator segments is shown qualitatively in curve 12. For example, referring again to FIG. 3, collimator segment 4e with the largest tomographic field of view 6e images with uniform sensitivity 12e in FIG. 4. Collimator segment 4d in FIG. 3 with tomographic field of view 6d images its smaller field of view with the same efficiency as collimator segment 4e, with the result that the combined imaging sensitivity in tomographic field of view 6d is greater than it is in tomographic field of view 6e, as shown in curve 12d of FIG. 4. By similarly combining the uniform sensitivities of multifield-of-view collimators, the cumulative sensitivity distribution 12 is obtainable.

By using collimators with different tomographic fields of view, varying sensitivities (uniform or non-uniform), and different types (parallel, converging and diverging) many continuous sensitivity distributions can be achieved as an approximation to virtually any desired continuous radial sensitivity distribution. Thus, in regions of particular interest in the imaged object, the sensitivity can be increased with respect to its value in other areas, thus increasing the signal to noise ratio in the measured data.

Figure 5A:
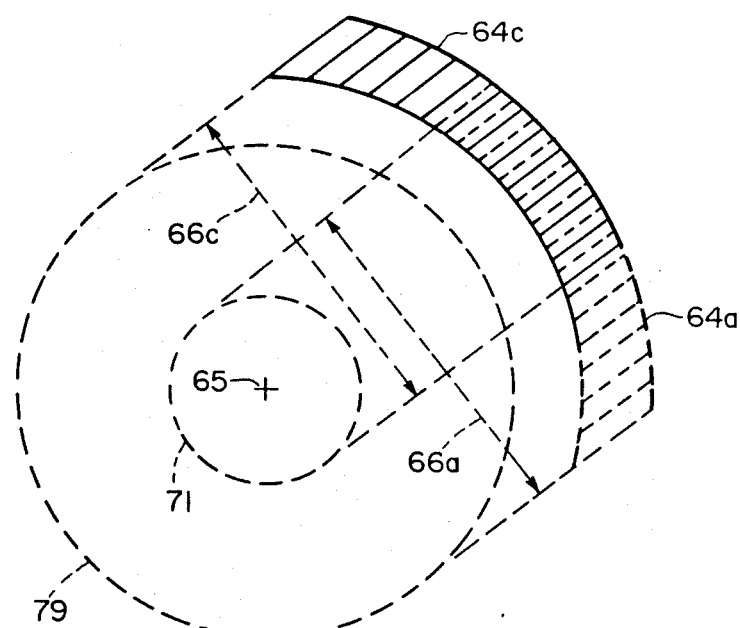
FIG. 5A is a schematic of two collimator segments of FIG. 5 aligned in parallel.
Figure 5B:
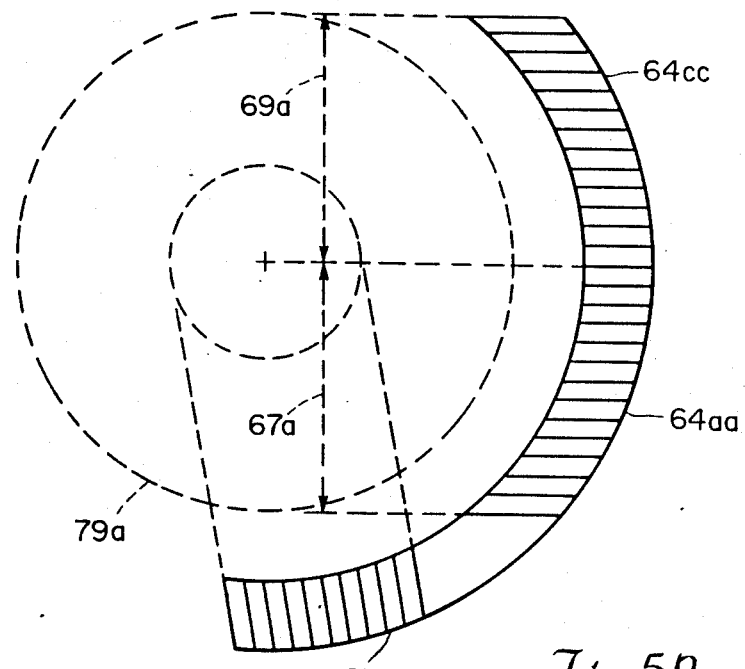
FIG. 5B is a schematic of the alignment of alternative collimator segments.
Figure 5:
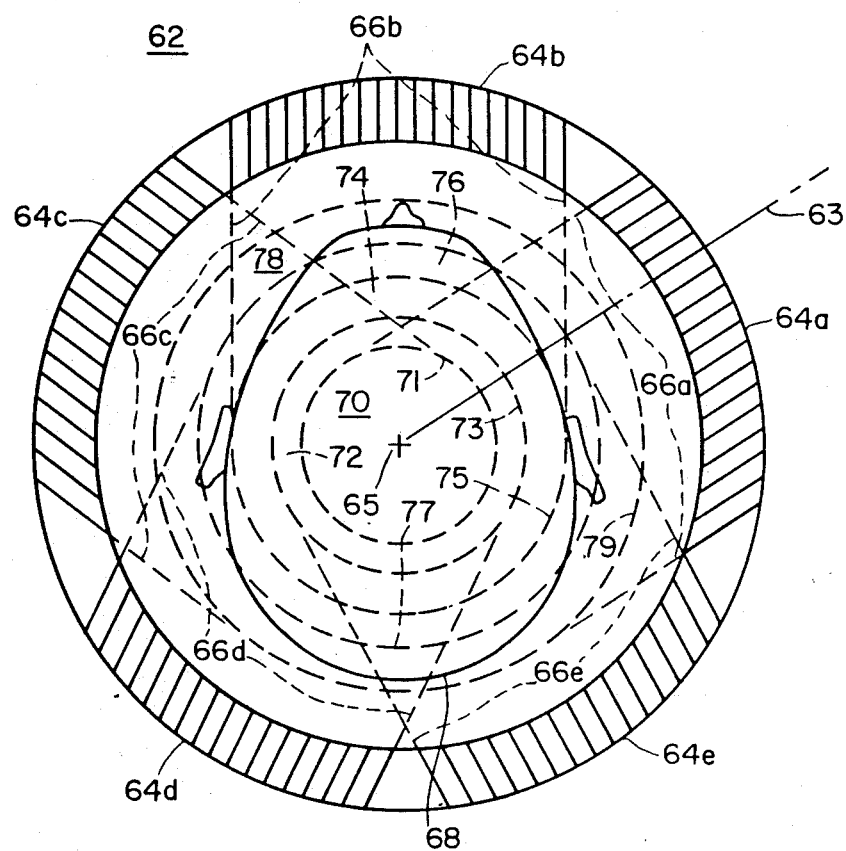
FIG. 5 is a multifield annular collimator system segmented into several parallel type collimator segments with different fields of view in which one of the boundaries defined by two collimator segments encompasses the object.

Multifield collimator system 62, FIG. 5, is another construction of a novel collimation system. Collimator system 62 is segmented into several parallel hole type collimator segments 64a, 64b, 64c, 64d, 64e having respective fields of view 66a, 66b, 66c, 66d, 66e which differ from each other, not one of which having a tomographic field of view large enough to encompass object 68. For example, field of view 66a encompasses all of tomographic field of view 70 but only portions of tomographic fields of view 72, 74, 76 and 78. Tomographic field of view 78 encompasses object 68; tomographic field of view 78 is defined by collimator segments 64a, 64c. Tomographic fields of view 70, 72, 74, 76 and 78 have respective boundaries 71, 73, 75, 77 and 79.

As stated above, the outer tomographic field of view boundary need not encompass the entire physical object itself. For example, collimators 64c and 64a can be eliminated such that collimator system 62 only collimates images within tomographic field of view boundary 77. The construction illustrated in FIG. 5, however, encompasses all of object 68 and provides unique image reconstruction.

As described below, one or more collimated images are collected through each collimator segment and matched with other collimated images collected at the same position, e.g. view position 63. Collimator segment 64a is shown at view position 63; segments with symmetrical fields of view about axis of rotation 65, e.g. segment 64b, are typically centered when at a view position.

Collimator segments 64a–64e share axis of rotation 65. The overlap of collimator fields of view 66a and 66c, for example, can be compared by rotating segment 64c about axis 65 until the edges of collimator field of view 66c are parallel with those of view 66a as shown in FIG. 5A. It is seen that fields of view 66a, 66c are staggered from each other but overlap in the region of inner boundary 71. The field of view defined by boundary 71 thus exhibits higher sensitivity than the remainder of the field described by the area between boundaries 71, 79.

Another construction of collimator segments is shown in FIG. 5B. Collimators. 64aa, 64cc can be constructed to have their fields of view, represented by arrows 67a, 69a, aligned to lie adjacent to each other at an inner point 65a shared both by the inner boundary and the axis of rotation of segments 64aa, 64cc while still defining in combination outer boundary 79. Imaging sensitivity is enhanced when a third collimator segment, e.g., segment 81, is added to overlap at least one of the other two fields of view.

Collimator 64a–64e, FIG. 5, provide the same sensitivity curve 12 as shown in FIG. 4. However, each collimator field of view 66a–66e contributes to curve 12 in a different manner. For example, the tomographic field of view between boundaries 6cc and 6dd, FIG. 3, is fully viewed by collimators 4d and 4e only. The tomographic field of view between boundaries 75 and 77, FIG. 5, however, is viewed by a combination of collimators 64a, 64c, 64d and 64e.

Figure 6:
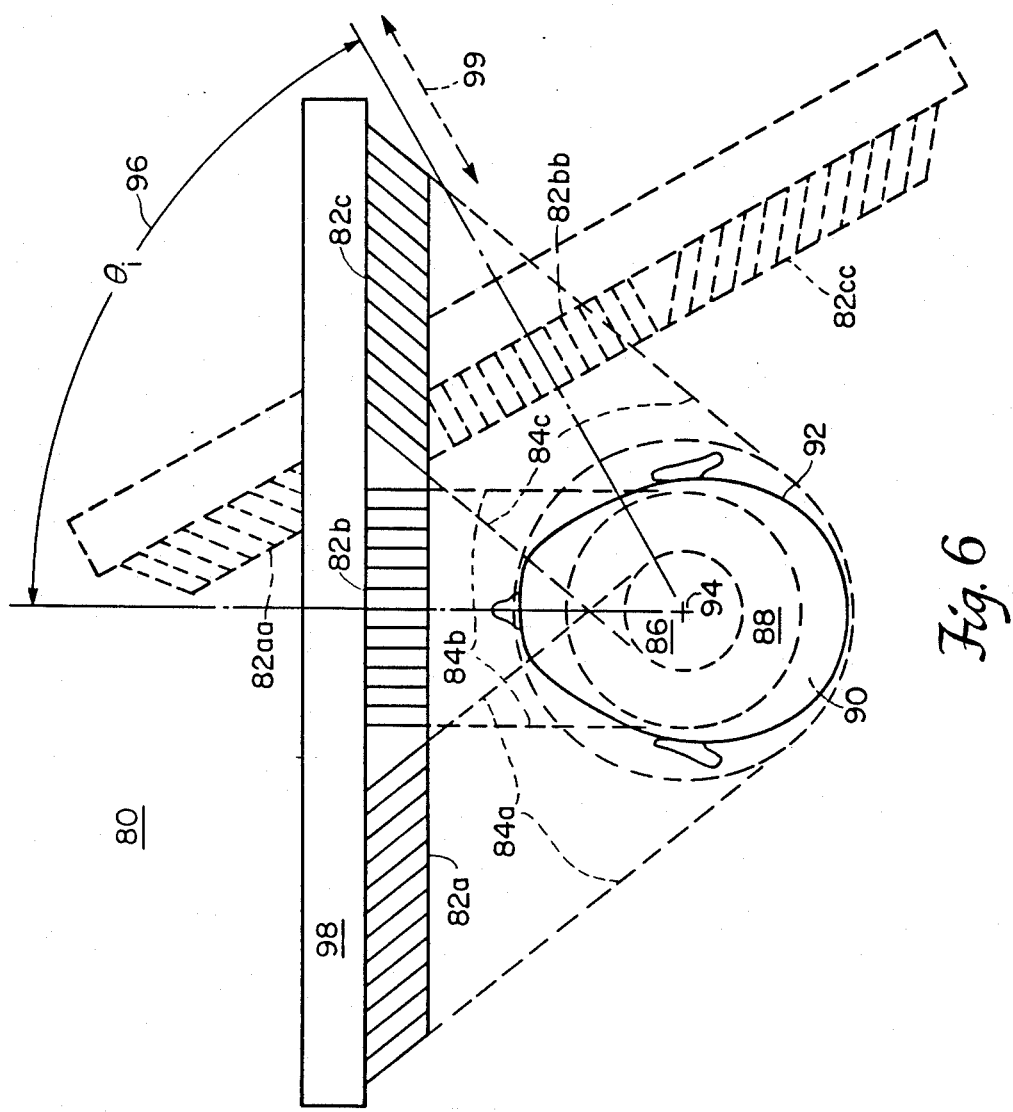
FIG. 6 is a multifield planar camera system segmented into three parallel type collimator segments having different fields of view in which one of the defined boundaries encompasses the object.

Multifield planar camera system 80, FIG. 6, comprised of position detector 98 and collimator segments 82a, 82b, 82c, illustrates another novel collimator arrangement. Collimator segments 82a, 82b and 82c provide collimator fields of view 84a, 84b, 84c, respectively which overlap in a manner that is similar to annular collimator system 62, FIG. 5, to produce concentric tomographic fields of view 86, 88, 90. Fields of view 84a, 84c of collimator segments 82a, 82c define tomographic field of view 90 which encompasses head 92.

Planar camera system 80 is rotated about axis 94 to obtain a number of views. Collimators 82aa, 82bb, 82cc, shown in phantom, represent the position of planar camera system 80 at angle of view $\theta_i$ shown by arrow 96. Similar collimator arrangements of other rotating camera systems such as the arcuate camera system disclosed in U.S. Pat. No. 4,095,107 can be utilized in similar fashion.

Both planar and arcuate camera systems can be translated, that is, moved radially toward or away from the object to be imaged. For example, planar camera system 80 in one Translation of a planar or arcuate camera system according to this invention results in tomographic field of view boundaries which are no longer circular.

Figure 7:
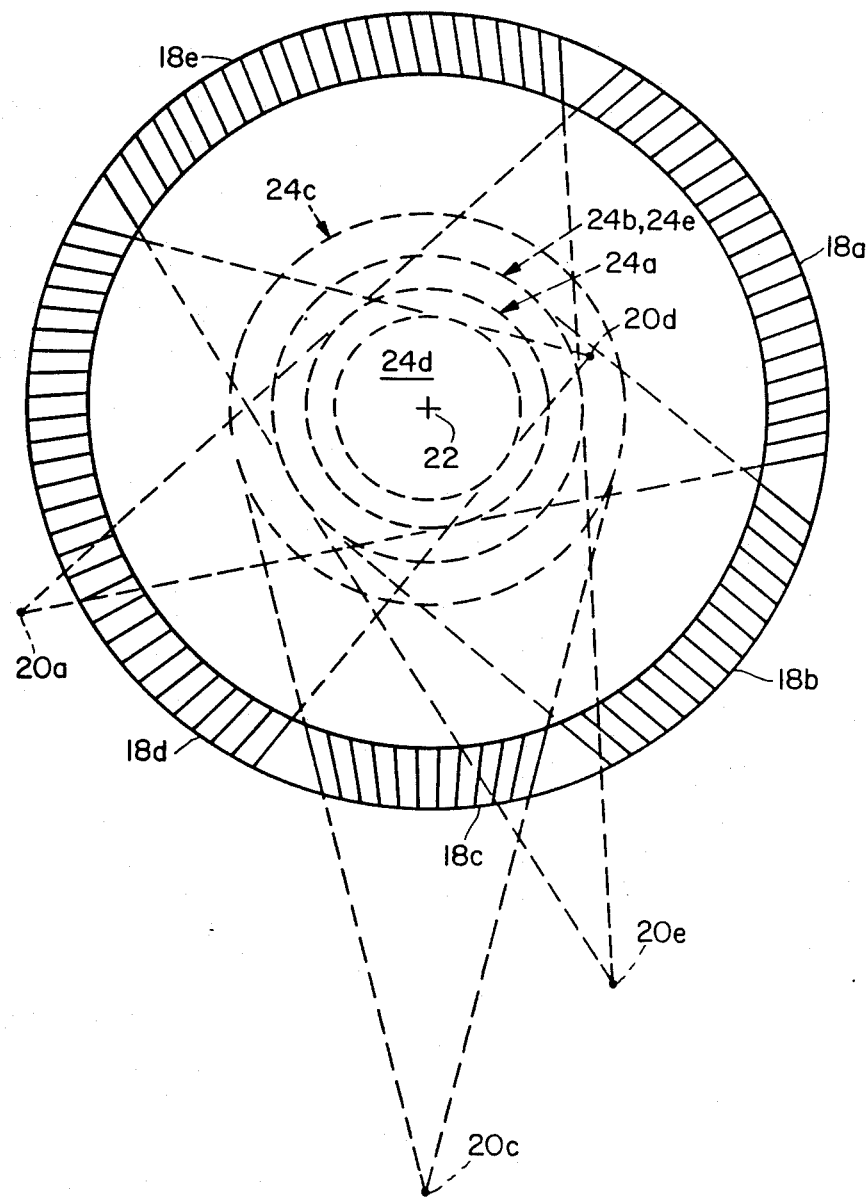
FIG. 7 is a multifield collimator system in which the collimator segments may define the same or different boundaries and have the same or different focal lengths.

FIG. 7 shows a multifield-of-view, or "multifield," annular collimator system according to this invention that utilizes several different types of collimator segments. Segment 18a is a convergent collimator segment whose axis of focus is marked by point 20a and whose tomographic field of view is 24a. Segment 18b is a parallel type collimator (focus axis at infinity) whose tomographic field of view is 24b. Segment 18c is a diverging type collimator whose axis of focus is at point 20c and whose tomographic field of view is 24c. Segment 18d is a converging type collimator with axis of focus at 20d and tomographic field of view 24d. And, segment 18e is also a converging type collimator with axis of focus at 20e and tomographic field of view 24e. Note that tomographic fields of view 24c, 24b and 24a are progressively smaller with the largest tomographic field of view 24c being at least as large as the imaged object while the others are smaller than the imaged object. Note also that tomographic fields of view 24b and 24e is the same size. By overlapping progressively more tomographic fields of view, the imaging sensitivity is increased. Thus, in the smallest tomographic field of view, 24d, the imaging sensitivity is greatest, while in tomographic field of view 24c, 24b and 24a the sensitivity progressively decreases. Dependent on design parameters, such as the cross-sectional area and length of the collimator channels as a function of position, the collimator segments 18 may each have uniform imaging sensitivity, or they may each have varying imaging sensitivity, and the composite sensitivity may be tailored to closely approximate a particular continuous sensitivity distribution. The image reconstruction of the data from such a multifocus collimator system may be accomplished by rebinning procedures similar to those conventionally used with convergent sampling collimators; see, e.g., G. T. Herman, *Image Reconstruction from Projections*, Academic Press, NY (1980).

Figure 8:
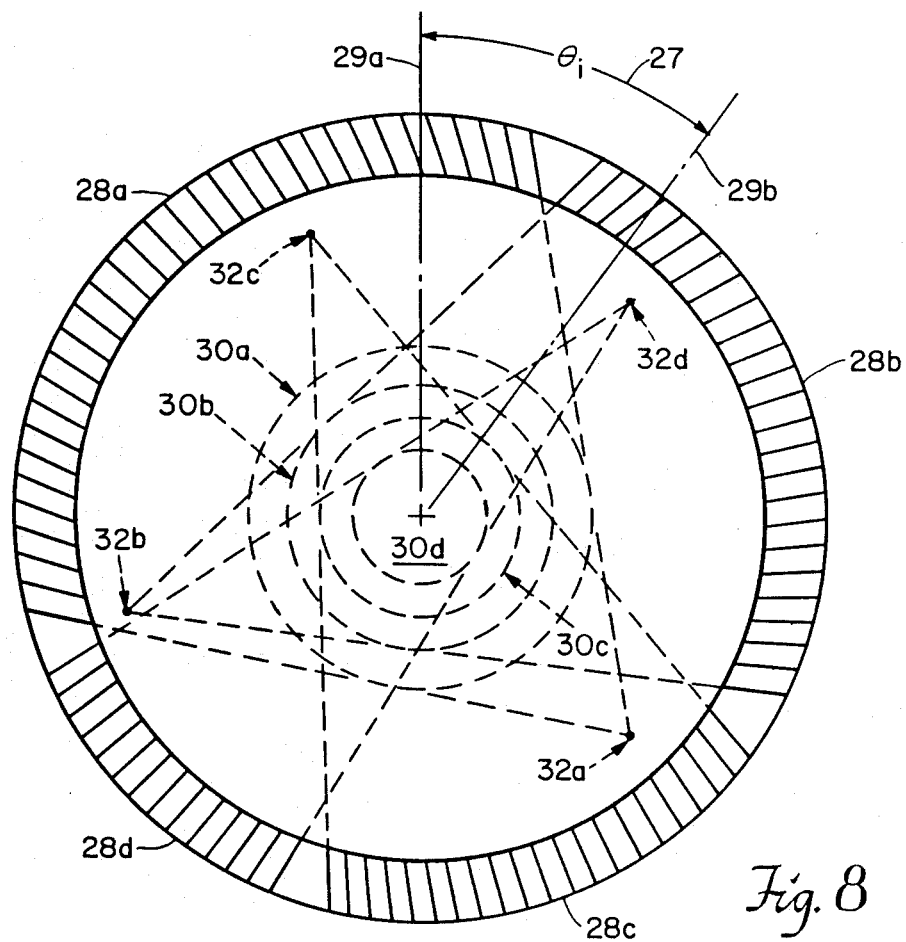
FIG. 8 is a multifield collimator system employing convergent type collimator segments each with the same focal length but defining different boundaries.

FIG. 8 shows a collimator system utilizing several converging collimator segments 28 each of which has the same focal length, but with different tomographic fields of view 30a, 30b, 30c, 30d. Collimator segment 28a has the largest tomographic field of view 30a, which is at least as large as the imaged object. Segment 28a has focal point 32a. Each of the collimator segments 28b, 28c and 28d has the same focal length or segment 28a, represented by focal points 32b, 32c and 32d, but has a progressively smaller tomographic field of view 30b, 30c and 30d, respectively, each of which is smaller than the imaged object.

Figure 8A:
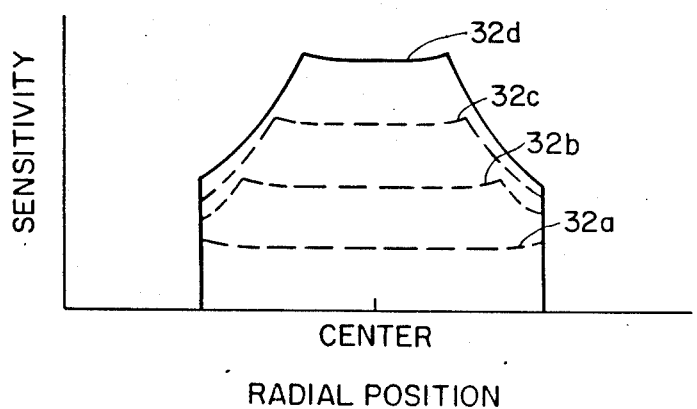
FIG. 8A is the associated composite sensitivity distribution for the collimator system of FIG. 8.

FIG. 8A shows a qualitative sensitivity curve as a function of radial position from the center of the imaged object corresponding to the collimator system of FIG. 8. Segment 28a, which views the entire imaged object, exhibits uniform sensitivity 32a in FIG. 8A, while segments 28b, 28c and 28d each contribute to increased imaging sensitivity in their respectively smaller tomographic fields of view as shown in continuous curves 32b, 32c and 32d, respectively, of FIG. 8A. The sensitivity curve of FIG. 8A is increased in the central portions of the imaged object, but other sensitivity distributions can be obtained with other collimator segment arrangements and various tomographic fields of view.

A three-dimensional multifield image of an object is acquired by combining the collimator image obtained from each collimator segment successively centered at each of N view positions distributed circumferentially about the object. The collimator structure of a radionuclide emission camera system such as described herein is rotated through N exposures to obtain the collimator images. A composite image is acquired at each of the N view positions; the N composite images from the N view positions are then combined to reconstruct a final three-dimensional image.

Figure 8B:
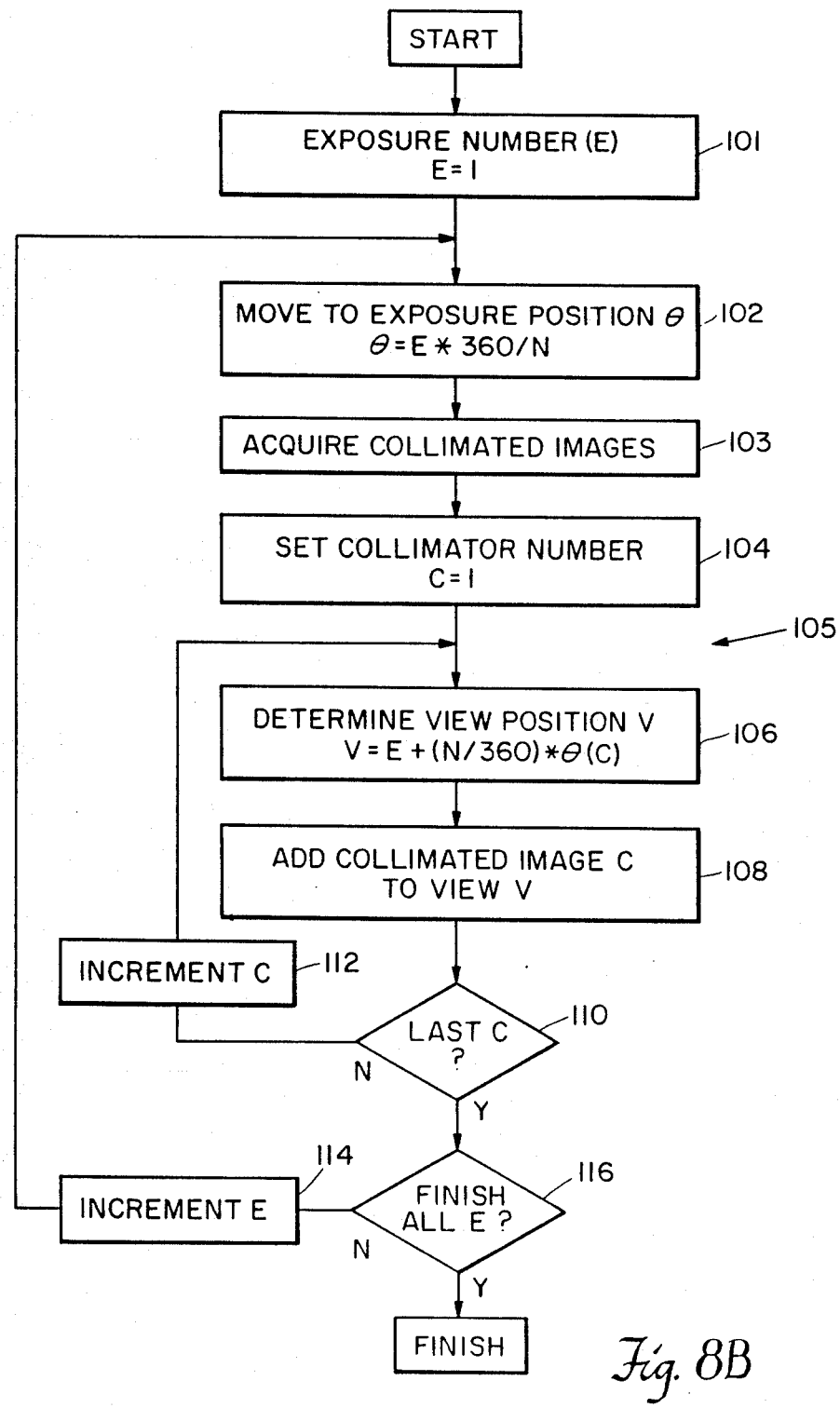
FIG. 8B is a flow chart of the operation that generates a final multifield image having the composite sensitivity distribution shown in FIG. 8A.

A collimator arrangement such as described herein, e.g., collimator segments 28a–28d, FIG. 8, can comprise a part of a radionuclide emission camera system such as shown in FIG. 1 of system is shown in FIG. 8B. The exposure number E is set to one, step 101, and the collimator structure is rotated to exposure position which is based upon the exposure number as determined by the formula $$\theta = E(360/N) \quad (1)$$

where N is the number of views to be obtained. Uniform angles are established between two successive exposures by equation (1) and the coordinate system is chosen so that the last exposure, the $N^{th}$, is at an angle of 360°; however, this arrangement of these parameters is not a limitation of the invention.

For each exposure position E, the collimator images are acquired, step 103, by measuring the radioactivity distributions falling through each collimator, such as collimators 28a–28d, FIG. 8.

After the data collection for exposure E is completed, loop 105 is entered whereby the image from each of the collimator segments is added to the final image. The collimator number C is initially set to one, step 104, and the view position V is determined in step 106 according to the formula $$V = E + (N/360)\theta(C) \quad (2)$$

View position V represents the memory location to which the C is then added to a memory location defined by view position V, step 108. In equation (2), a view number greater than N is considered to be that number less N. For example, if view number V has a value of N plus three, the view position to which the collimator image would be added is view three.

Loop 105 is continued by determining, step 110, if collimator number C is the last number, e.g., segment 28d, and incrementing the collimator number, step 112, until the last collimator number is reached. When all the collimator images have been added to their appropriate view positions, the exposure number is incremented, step 114, unless it is determined that a total of N exposures has been taken, step 116.

Figure 9:
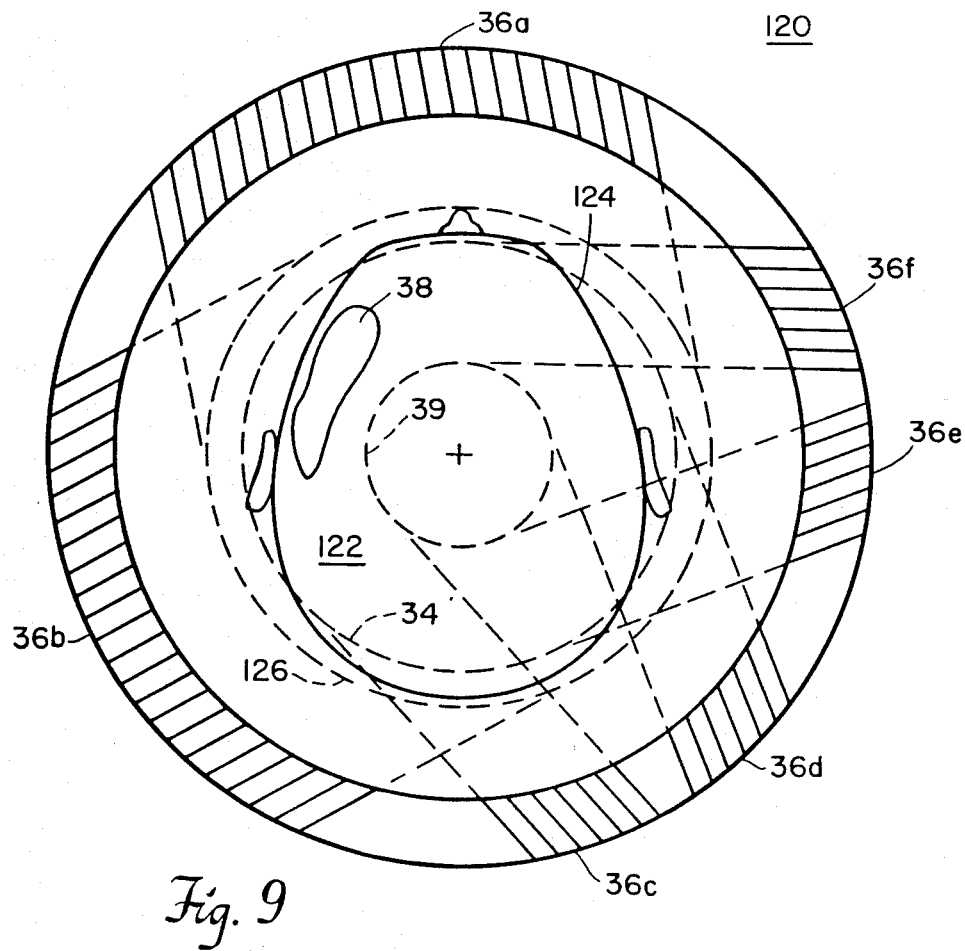
FIG. 9 is a multifield collimator system in which axially parallel type collimator segments are employed in order to enhance the imaging sensitivity in a peripheral annular region of the imaged object.

Collimator system 120, FIG. 9, provides increased imaging sensitivity in a peripheral region 122 between cross-sectional boundaries 34 and 39. Collimator segments 36a and 36b encompass object 124 and each define cross-sectional boundary 126. The collimator fields of view of collimators 36c, 36d, 36e and 36f, however, overlap only in peripheral region 122 which is toroidal in this construction.

Figure 9A:
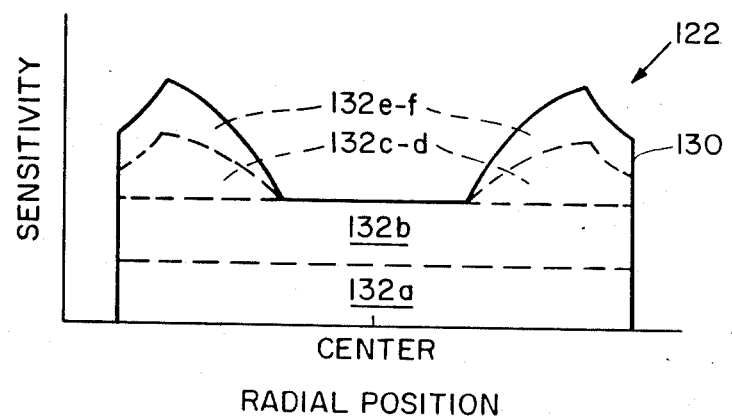
FIG. 9A is the associated composite sensitivity distribution for the collimator system of FIG. 9.

Within imaged object 124 is area of interest 38 such as a peripherally located region in the human brain. As shown in FIG. 9A, enhanced imaging sensitivity in peripheral region 122 is provided by collimator system 120 when each collimator segment 36a–36f has uniform imaging sensitivity. Sensitivity curve 130 illustrates the sensitivity as a function of radial position from the center of the imaged object. Imaging sensitivities 132a–132f represent the composite radial sensitivities of collimator segments 36a–36f, FIG. 9. The central portion of sensitivity curve 130 represents a low sensitivity since only the collimator fields of view of collimators 36a, 36b overlap in this region. In peripheral region 122, however, collimators 36c, 36e are aligned to overlap and collimators 36d, 36f are aligned to overlap a second radial portion to provide higher sensitivity established by segments 36a, 36b for the central region.

The system of FIG. 9 is yet another example of the method by which the imaging sensitivity may be varied as a function of radial position from the center of the imaged object. The method include aligning at least two fields of view to define at least two tomographic field of view boundaries, one of which encompasses the object. Several fields of view from several collimator segments, each of which may have uniform or non-uniform imaging sensitivity, and each of which may be parallel, converging or diverging, can be overlapped according to the desired imaging sensitivity.

Figure 10:
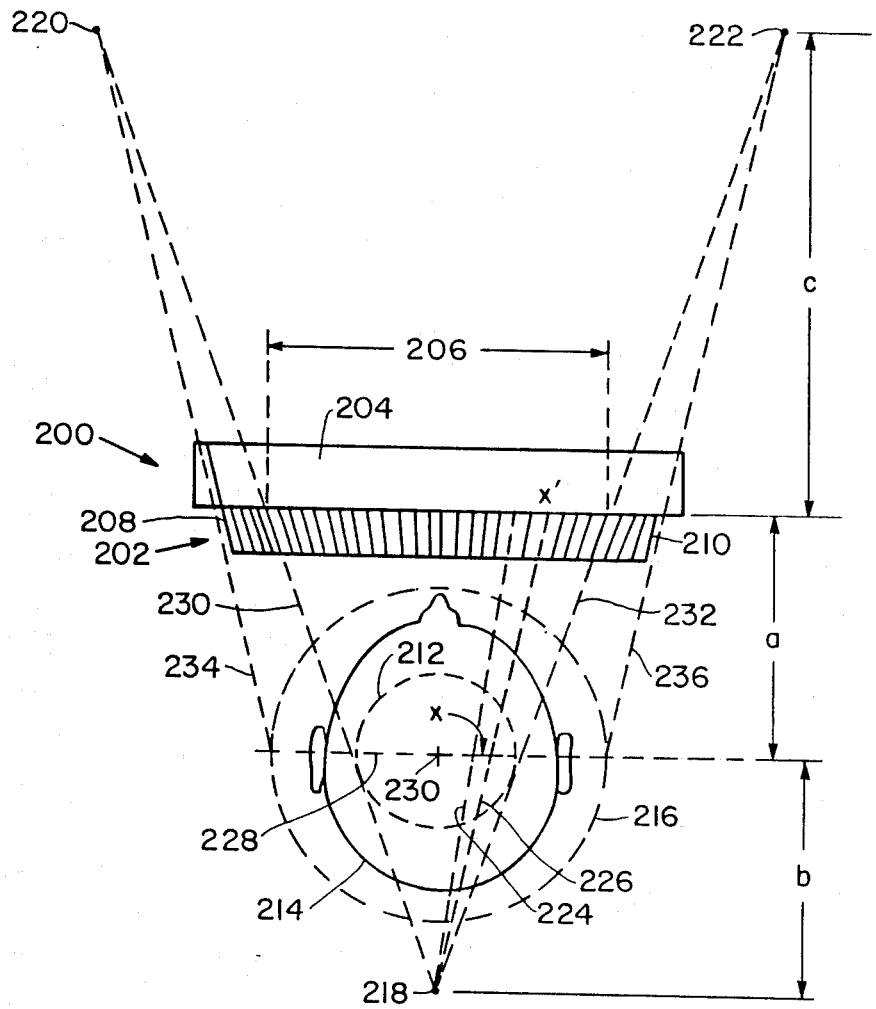
FIG. 10 is a schematic diagram of a novel compound collimator system having two sections which define

Compound collimator system 200, FIG. 10, includes collimator structure 202 behind which is located position detector 204. Collimator structure 202 is divided into central converging section 206 which is bounded by a second, divided section composed of sections 208, 210 which are diverging collimators. Section 206 has a tomographic field of view which defines inner tomographic field of view boundary 212 about the inner portion of head 214. Diverging sections 208, 210 define tomographic field of view boundary 216 which encompasses head 214. Converging section 206 focuses positively to point 218 while diverging sections 208, 210 focus negatively to points 220, 222, respectively.

Converging section 206 provides both greater sensitivity and greater inherent resolution which is illustrated as follows. Length x, located between dashed lines 224, 226 at the intersection of line 228 which is a diameter line passing through axis of rotation 230, is magnified to length x' at distance a, corresponding to the forward face of detector 204. Focal point 218 of converging section 206 is distance a+b from detector 204. Projections along diameter line 228 within tomographic field of view boundary 212 are magnified by the ratio of their respective distances, that is, by $(a+b)/b$.

Both sensitivity and inherent resolution are improved proportionally to the magnification defined by the above ratio. In the absence of attenuation, the sensitivity of a tomography camera is proportional to the fraction of radiation received by the camera of the total radiation emitted from the radionuclide source distribution. The inherent resolution, or effective intrinsic resolving power, is the ability of the detector to resolve two events striking its surface.

While a converging collimator improves both sensitivity and inherent resolution, the converging collimator is by its nature much larger in size than that of a corresponding parallel collimator, such as is evident by comparing parallel collimator 5a, FIG. 1, with converging collimator 43a, FIG. 2. Further, the detector must be correspondingly large to gather the collimated data. Compound collimator 202 achieves high imaging sensitivity within tomographic field of view boundary 212 while minimizing the length of detector 204 by imaging the remaining portion of head 214 utilizing diverging collimator sections 208, 210.

One technique of constructing compound collimator 202 is as follows. Tomographic field of view boundaries 212, 216 are defined such that boundary 212 encompasses a portion to be imaged at a greater imaging sensitivity, and boundary 216 is defined to encompass head 214 which is the object to be imaged. The selected imaging sensitivity for converging section 206 determines focal point 218; section 206 is bounded by lines 230, 232 intersecting at focal point 218. To minimize the overall length of detector 204, boundary lines 230, 232 are extended negatively as are lines 234, 236 which are tangent to outer boundary 216. The boundary lines intersect at negative focal points 220, 222, respectively, at distance c from the forward face of detector 204. Along diameter line 228 between boundary lines 212 and 216, the magnification is equal to $c/(a+c)$.

The net sensitivity at any point within boundaries 212, 216 is given by the average of the sensitivities attributable to that point as collimator system 200 is positioned sequentially about axis of rotation 230. The collimator sections operate in combination: for example, collimator sections 108, 210 corresponding to the portion for which tomographic field of view boundary 216 is defined establish, in combination with the sections, e.g. section 206, having collimator fields of view overlapping that portion, a different imaging sensitivity for that portion. The inner collimator sections typically have collimator fields of view which overlap the fields of view of peripheral collimator sections.

Figure 11:
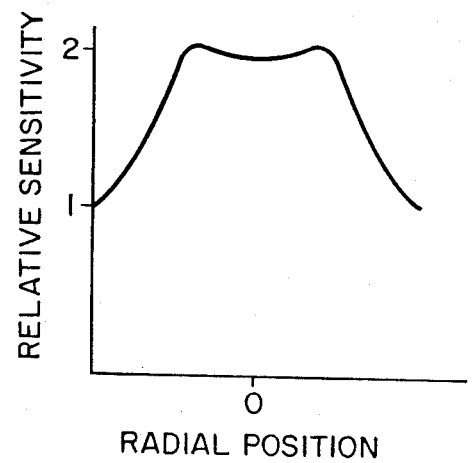
FIG. 11 is a graph of the relative sensitivity distribution for the compound collimator system of FIG. 10.

A sensitivity profile through diameter line 228 in relation to radial position is shown in FIG. 11. The circularly symmetrical sensitivity profile is highest in the central regions of the tomographic field of view and lowest at the periphery. Within boundary 212, which is viewed only by converging section 206, the sensitivity is nearly constant, varying between 2.0 and 2.1. Progressing radially outward thereafter, the sensitivity diminishes to approximately 55 percent of its peak value at the edge of boundary 216. In another construction in which diverging sections 208, 210 occupy a larger fraction of the total field, the sensitivity at the periphery will be even lower because the lower sensitivity diverging collimators contribute more strongly to the admixture of sensitivities at the edges of the field.

Computerized tomographic reconstruction from parallel projections is accomplished by rebinning of detector data collected at different viewing angles. The data collected at different viewing angles from a mixture of non-parallel projected gamma rays, that is, with converging and diverging collimators, is accomplished by reorganizing the data into sets of parallel projected data as is well known in the art.

Figure 12:
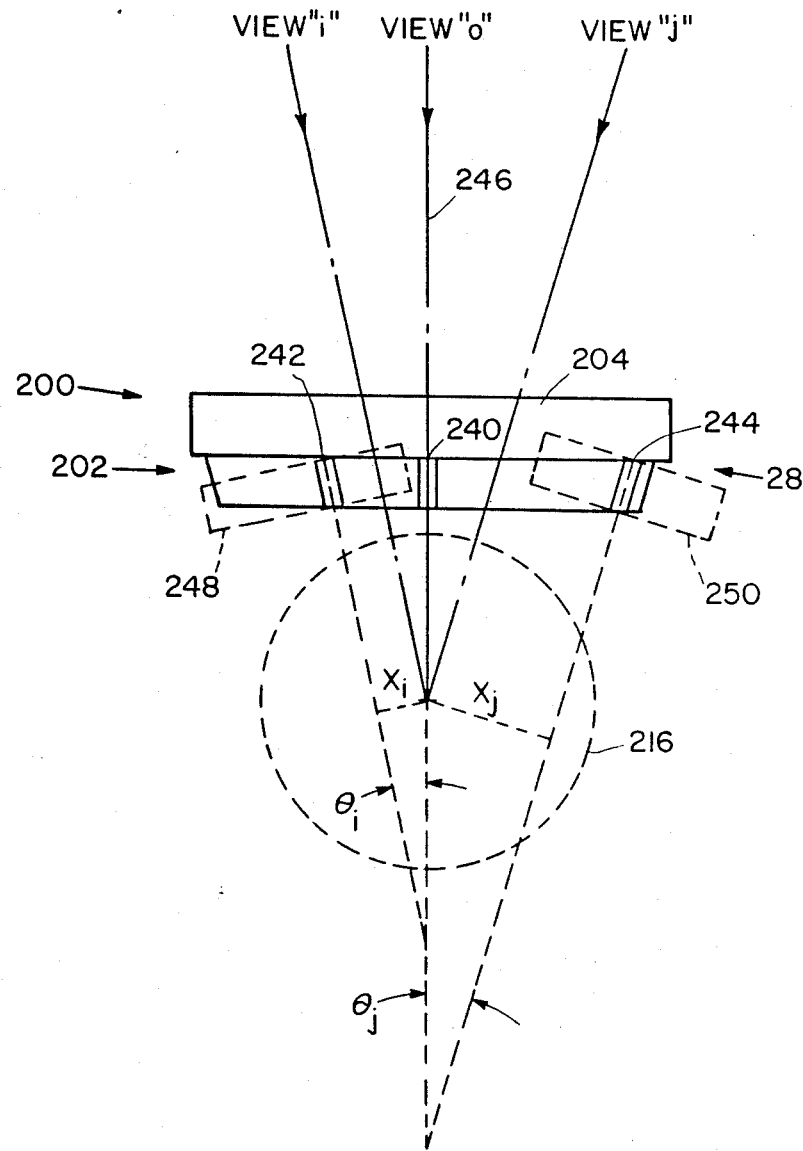
FIG. 12 is a schematic of the collimator system of FIG. 10 illustrating the organization of detector data for rebinning.
Figure 13:
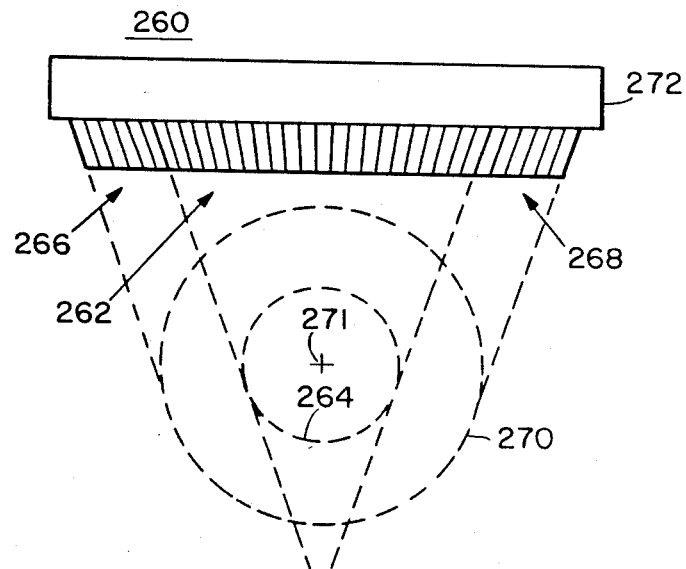
FIG. 13 is a schematic diagram of yet another compound collimator system having a converging center section and a divided parallel collimator section on either side of the converging section.

Rebinning is illustrated in FIG. 12 for collimator elements 240, 242 within converging section 206 and collimator element 244 within diverging section 210. Collimator structure 202 is positioned at detector viewing position "0" with its center line 246 at $\theta=0$. At this position, all other collimator elements view within boundary 216 at a different angle. For example, collimator element 242 views the portion represented by imaginary parallel collimator 248, shown in phantom. Similarly, diverging collimator element 244 views the portion within boundary 216 at view position $\theta_j$, represented by imaginary parallel collimator 250. Data collected through collimator elements 242, 244 therefore contribute to the $\theta_i$ and $\theta_j$ set of parallel projections at distances $x_i$ and $x_j$, respectively, from the central line of each imaginary parallel collimator. The various views are summed as collimator system 200 is rotated until all bins are filled.

Other compound collimators according to this invention have different combinations of collimator sections. Collimator system 260, FIG. 13, includes converging section 262 which defines boundary 264, and parallel collimator sections 266, 268 which define boundary 270. The sensitivity at the periphery is thereby increased relative to collimator system 200, FIG. 10, but a slightly larger positioned detector 272 is required to accommodate the added collimator surface as necessitated by parallel hole collimator sections 266, 268.

Boundaries 264, 270 need not be circular about axis of rotation 271. For example, in another construction, collimator system 260 is translatable radially relative to axis of rotation 271 to define boundaries 264, 270 which are no longer circular.

Figure 14:
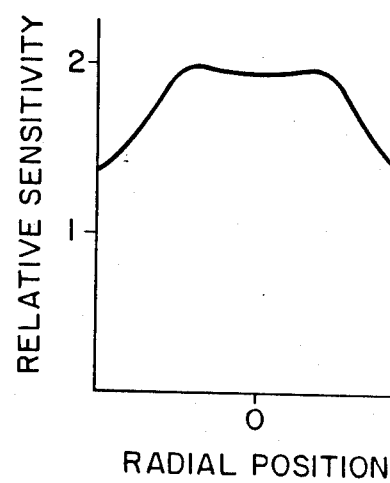
FIG. 14 is a graph of the relative sensitivity distribution for the collimator system of FIG. 13.
Figure 15:
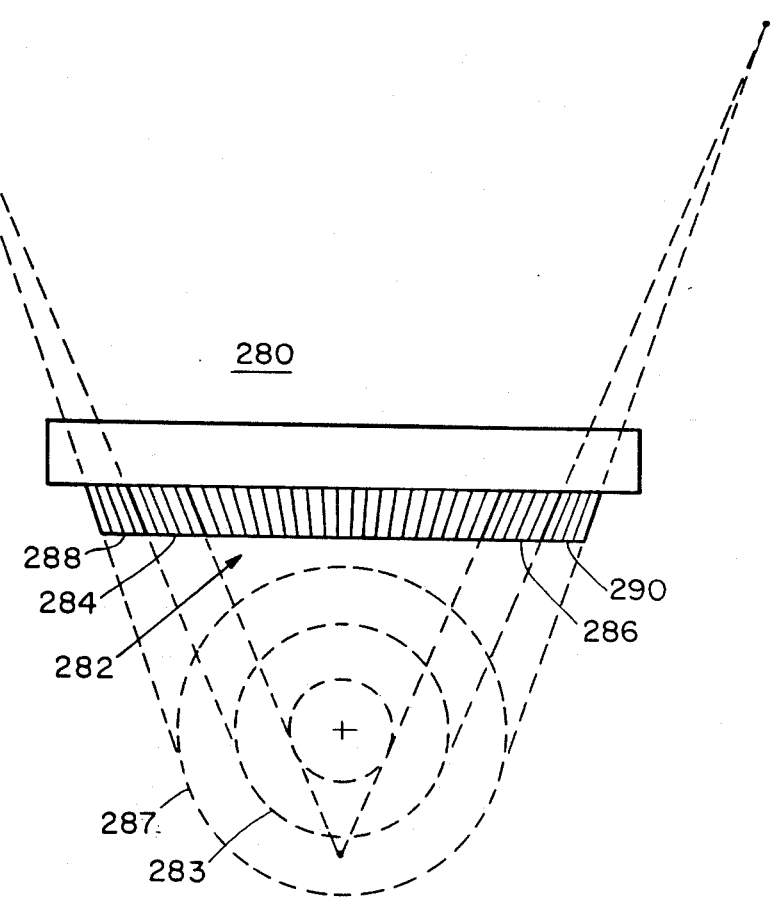
FIGS. 15-18 are schematic diagrams of yet other constructions of compound collimator systems.

The relative sensitivity distribution for collimator system 260 is shown in FIG. 14. The sensitivity profile in the central region is approximately equal to that of collimator system 200, because similar converging collimator sections are utilized in both constructions. Toward the periphery, however, where the sensitivity is an admixture of collimator viewings, the sensitivity diminishes to about 67 percent of its central value. collimator sections. Central section 282 is highly converging which generates increased magnification and in turn provides increased imaging sensitivity and intrinsic resolution. Tomographic field of view boundary 283 is defined by parallel sections 284, 286, and outer boundary 287 is defined by diverging sections 288, 290.

The central collimator section of a compound collimator according to this invention need not be converging, and the region with the highest imaging sensitivity can lie in the outer portion of the object. Collimator system 300, for example, FIG. 16, has central parallel section 302 and outer converging sections 304, 306 which provide higher imaging sensitivities between boundaries 308, 310 for collimator system 300. The relative sensitivity is 1.0 within boundary 310 and increases toward the periphery.

Figure 17:
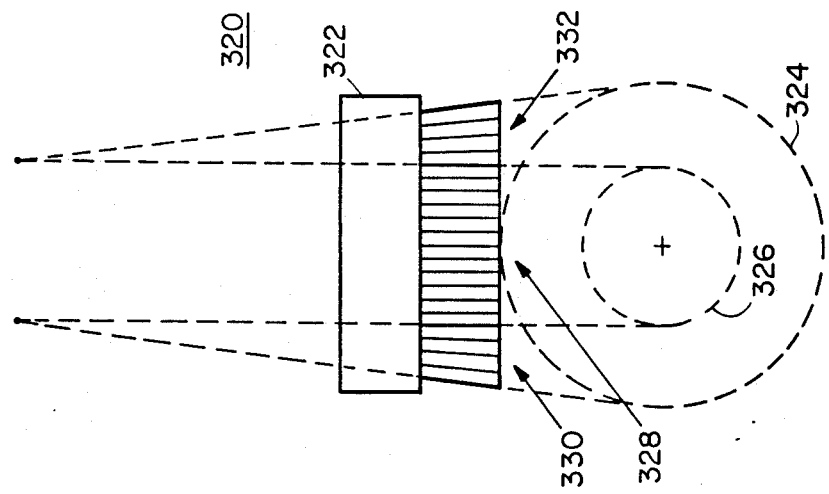
Figure 16:
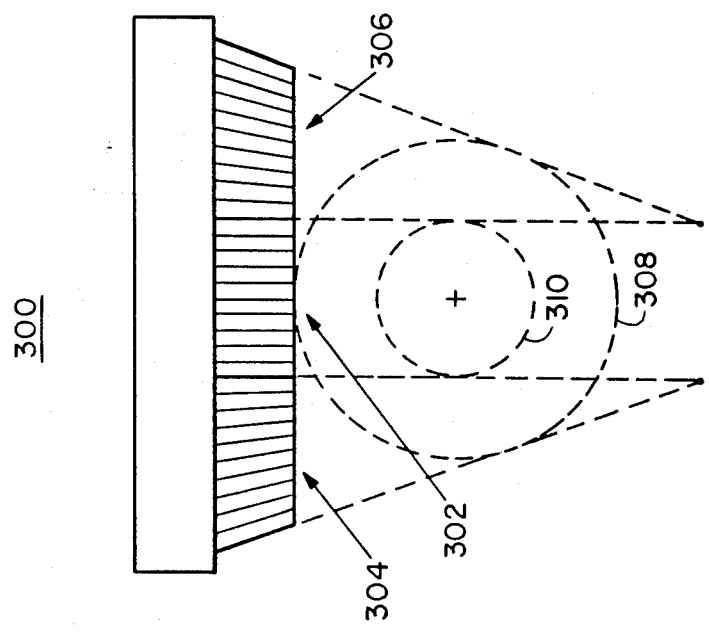

Collimator system 320, FIG. 17, utilizes detector 322 which is smaller than tomographic field of view boundary 324. Nonetheless, collimator system 320 achieves the viewing of the portion within boundary 326 at the imaging sensitivity of a parallel collimator. This is accomplished using central parallel section 328 and outer diverging sections 330, 332.

Figure 18:
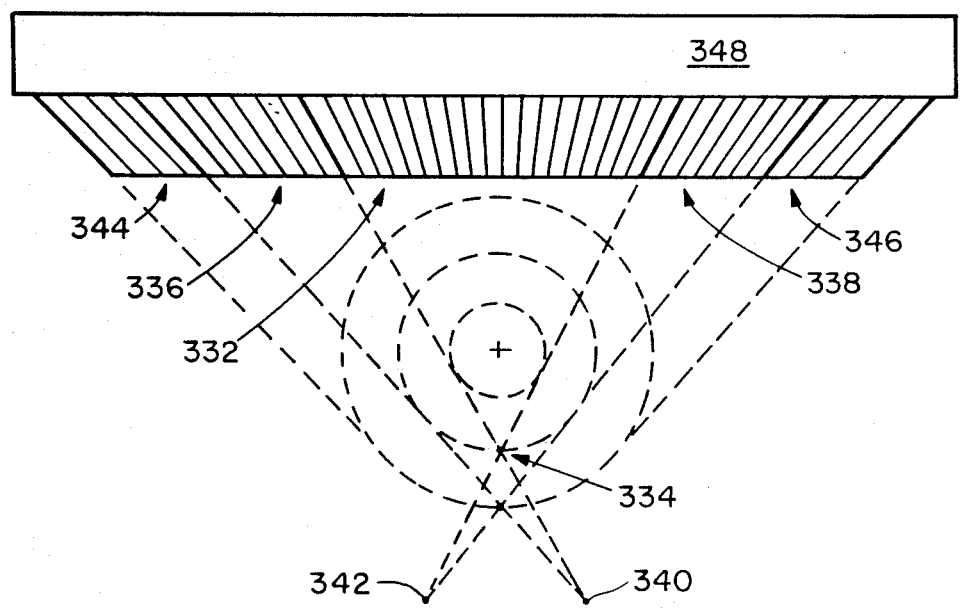
Figure 20:
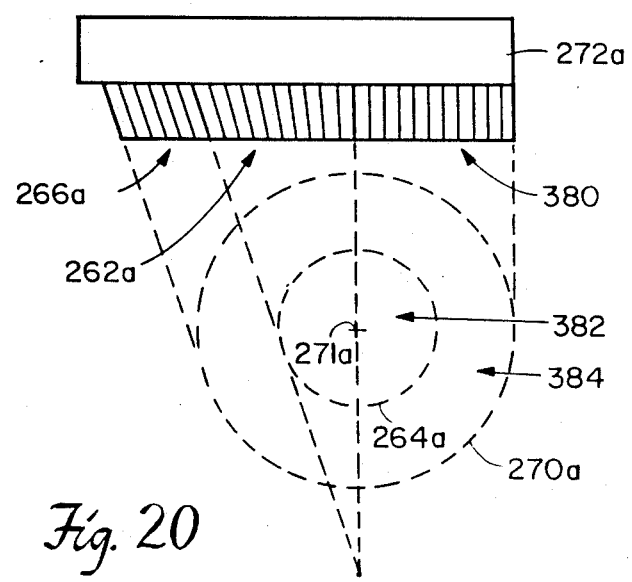
FIG. 20 is a schematic diagram of another compound collimator system having asymmetric collimator sections.

Very high imaging sensitivities are provided by collimator system 330, FIG. 18, having central strongly converging section 332 which focuses to point 334, and less strongly converging sections 336 and 338 which focus to points 340, 342, respectively. The outer portion of the region to be imaged is viewed by parallel sections 344, 346. Collimator system 330 is particularly useful when viewing a small object such as a brain, when a large position detector 348 can be accommodated.

Collimator system 350, FIG. 19, illustrates a modification of collimation system 330, FIG. 18, for use in a rotating annular collimator system with fixed position detector 360. Central converging section 332a focuses to point 334a, sections 36a, 338a focus to points 340a, 342a, respectively, and parallel sections 344a, 346a view the portion within outer tomographic field of view boundary 362. In addition, separate collimator segment 364 defines boundary 366 which overlaps boundaries 367, 369 defined by sections 332a, 336a, 338a, and part of the field of view of parallel sections 344a, 346a. Enhanced imaging sensitivity is provided in the region of overlap.

Compound collimators need not be symmetric. Collimator system 260a, FIG. 20, rotates about axis of rotation 271a and includes converging section 262a which defines boundary 264a, and parallel collimator section 266a which defines boundary 270a. In addition, collimator system 260a further includes parallel collimator section 380 which has a collimator field of view that overlaps both portions 382, 384 within boundaries 264a, 270a, respectively. Section 380 enables detector 272a to be shorter in length than detector 272, FIG. 18.

Collimator systems according to this invention vary the imaging sensitivity along the dimension parallel to the axis of rotation. In some constructions the imaging sensitivity is also varied in a plane normal to the axis of rotation as described above. Collimator system 400 according to this invention, FIG. 21A, provides converging focus in two dimensions. Radionuclide emissions from within head 402 are restricted and collimated by collimator 404 and detected by detector 406. Collimator system 400 is a planar collimator rotatable about axis of rotation 408. Collimator elements 410 converge to focal line $F_1$, that is, the axes of collimator elements 410 converge in a plane normal to axis of rotation 408. The axes of collimator element 410 also converge in a plane parallel to axis of rotation 408 and focus at focal line $F_2$. Collimator element 412, for example, is oriented toward focal point 414 while collimator element 416 is oriented toward focal point 416.

Figure 21B:
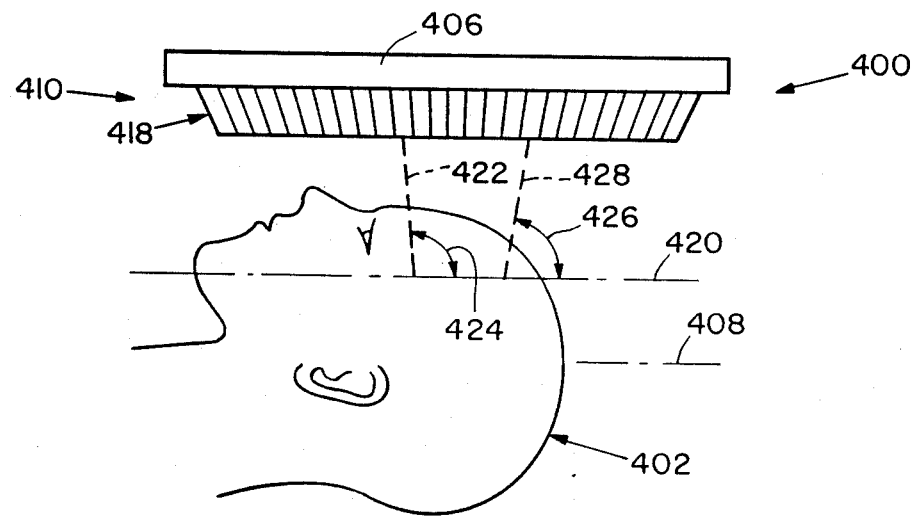
FIGS. 21B and 21C are side and end views, respectively, of the collimator system of FIG. 21A showing one of the lines intersected by the collimator element axes.

The focusing of collimator system 400 in the dimension parallel to axis of rotation 408 is shown in FIG. 21B. Row 418 of collimator elements 410 contains collimator elements whose axes intersect line 420 at different angles. Collimator element axis 422, for example, intersects line 420, which is parallel to axis of rotation 408, at angle 424 which is different from angle 426 formed by the intersection of collimator element axis 428 and line 420. Consequently, imaging sensitivity increases approaching the focal point of the field of view of collimator system 400. Further, imaging sensitivity is uniformly higher along line 420 than the sensitivity provided by a conventional collimator whose collimator element axes would intersect line 420 all at the same angle.

Figure 21C:
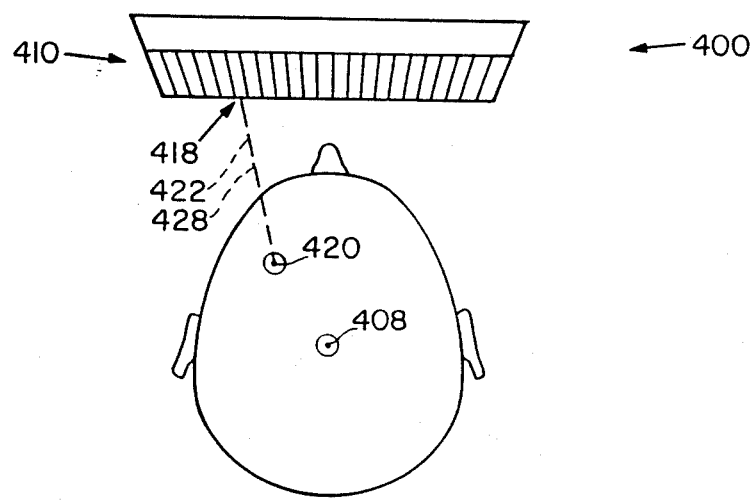

An end view of collimator system 400 is provided in FIG. 21C to further illustrate the relationship among line 420, axis of rotation 408, and collimator element row 418. The actual distance of line 420 from collimator 410 is not important; collimator element axes 422, 428 intersect at different angles any line parallel to axis of rotation 408 and within their 410 may provide uniform imaging sensitivity in a plane normal to axis of rotation 408, such as shown by combining collimator elements 40b, FIG. 3C of Genna et al., U.S. Pat. No. 4,584,478, with collimator elements 150, FIG. 8 of that patent.

Figure 22:
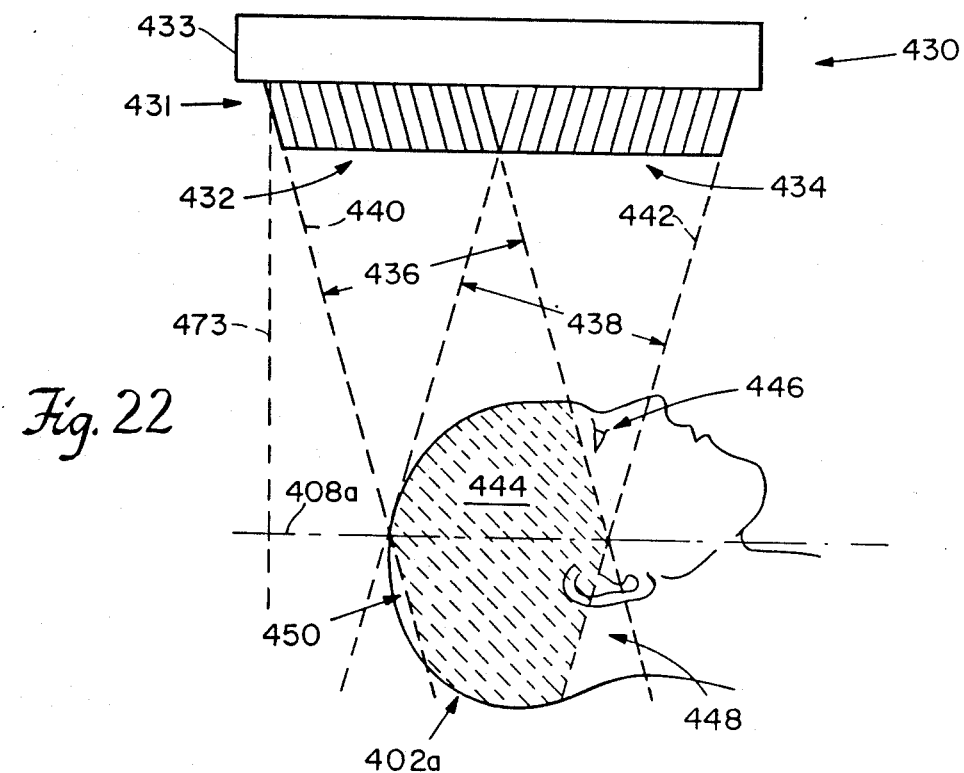
FIG. 22 is a schematic side view of a collimator system according to this invention having the focusing characteristics of a multifield collimator in the plane containing the axis of rotation.

Collimator system 430 according to this invention, FIG. 22, exhibits the focusing characteristics of a multifield collimator along the dimension parallel to axis of rotation 408a. Collimator elements 431 are arranged in two sets, each set corresponding to one of collimator segments 432, 434 having segment field of views 436, 438, respectively. The collimator field of view of collimator system 430 lies between dashed lines 440, 442 between detector 433 and axis of rotation 408a.

In some constructions a collimator system according to this invention exhibits complex focusing characteristics in both dimensions. For example, collimator system 430, having multifield characteristics established by segments 432, 434, can be combined with collimator system 200, FIG. 10, in the dimension normal to axis of rotation 408a.

The region of overlap of segment fields of view 436, 438 establishes enhanced imaging sensitivity in region 444 relative to regions 446, 448, and 450. Portion 444 is viewed by both collimator segments 432, 434 through 360° rotation. In contrast, portions 446, 448, 450 provide less complete information because they are not continuously viewed by the same collimators. For example, segment 434 views portion 446 in the viewing position shown in FIG. 22; when rotated 180°, however, the view of segment 434 includes portion 448 and not portion 446. Within portion 444, the imaging sensitivity is approximately twice that which would be provided by a conventional parallel type collimator in this dimension.

Figure 23A:
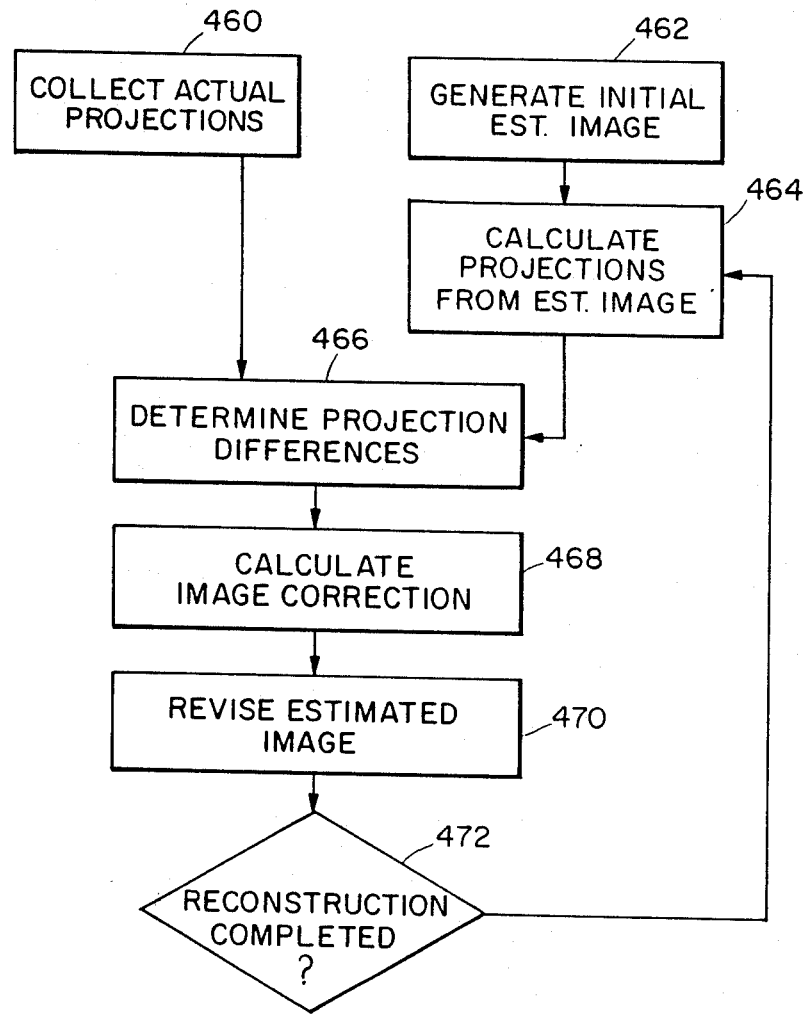
FIGS. 23A and 23B are flow charts of a general iterative reconstruction procedure for the collimator system of FIG. 22.

Collimated images collected through collimator elements 431 are combined to produce a final image of head 402a exhibiting the selected variation in imaging sensitivity established by collimator segments 432, 434. One procedure for reconstructing the image of head 402a is shown in FIG. 23A. Actual projections are collected, step 460, and an initial estimated image is generated, step 462. Several techniques for generating estimated images are described in G. T. Herman, *Image Reconstruction from Projections,* Academic Press (1980). The closeness of the estimated image to the actual image affects the speed and accuracy with which the estimated image is made to converge with the actual image. The estimated image may initially be a uniformly gray distribution of intensity equal to the average intensity observed, or may have a uniform image of zero intensity. Another technique is described below in FIG. 23B. Projections are then calculated that would be measured from the estimated image by the actual geometry of the collimator elements, step 464. If the estimated image were calculated in step 464 would be identical to actual projections collected in step 460. Differences between the projection differences are determined in step 466, and a new set of projections equivalent to the differences between the calculated projections and the actual projections is established. A three-dimensional image correction is generated by performing unfiltered back projection of the projection differences, taking into account the actual geometry of the collimator elements. The image correction obtained in step 468 is multiplied by a scalar factor, known as a convergence factor, and is added to the estimated image to revise the estimated image, step 470. If the reconstruction is not completed, the procedure returns to step 464 and continues until a certain number of iterations have been performed or until the estimated image converges to an acceptable level, e.g., the average projection differences are below a predetermined value.

Figure 23B:
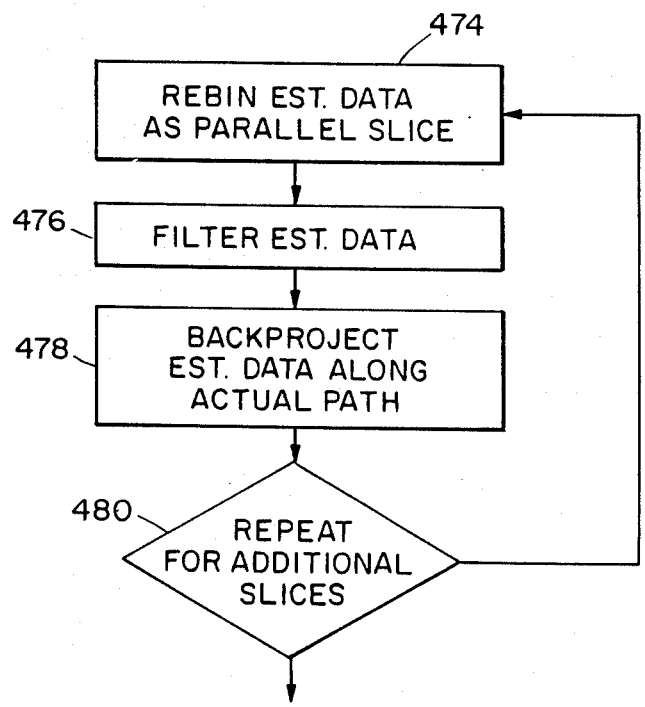

A more detailed technique of generating the initial estimated image is shown in FIG. 23B. The data collected by position detector 433, FIG. 22, can be grouped as a series of parallel slices, such as the slice indicated by dashed line 473 which represents a plane normal to axis of rotation 408a. The estimated data is rebinned to match rebinning of the collected data as described above in relation to FIGS. 8B and 12. The estimated data is then filtered, step 476, and back projected, step 478, along the actual path defined by the orientation of the collimator elements. Each volume element, hereinafter referred to as a voxel, within the estimated image is divided by a number proportional to the density of the back projections in that voxel. In FIG. 22, for example, voxels in portion 444 receive approximately twice as many data positions during back projection as the voxels in portions 446, 448, and 450. The procedure is repeated for additional slices progressing along axis of rotation 408a, step 480, until a full three-dimensional estimated image has been generated.

Figure 24A:
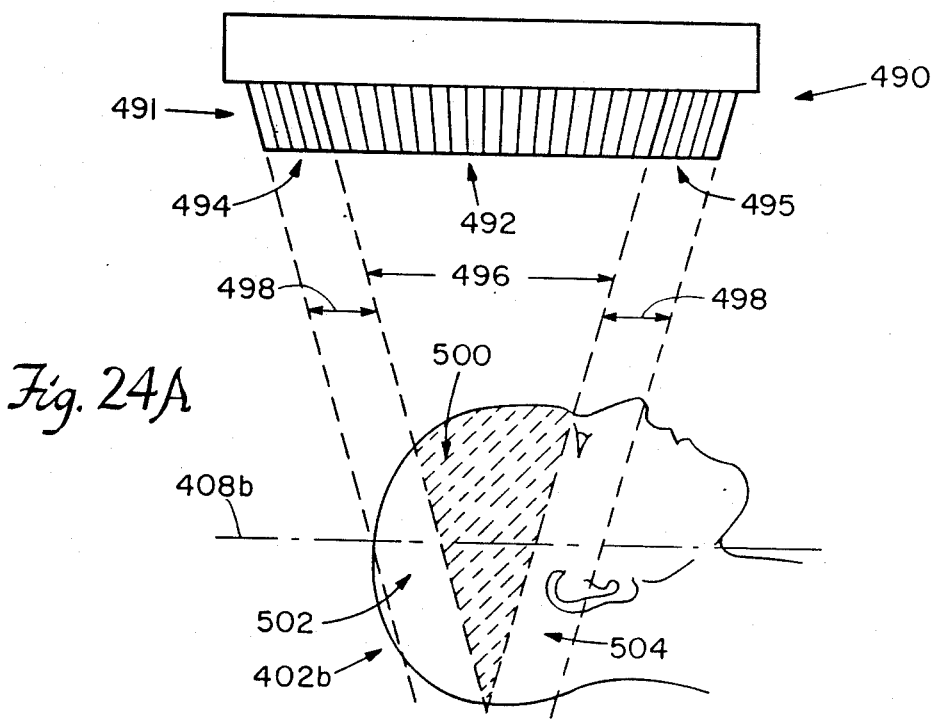
FIG. 24A is a schematic side view of an alternative collimator system according to this invention having the focusing characteristics of a compound collimator in the plane containing the axis of rotation.
Figure 24B:
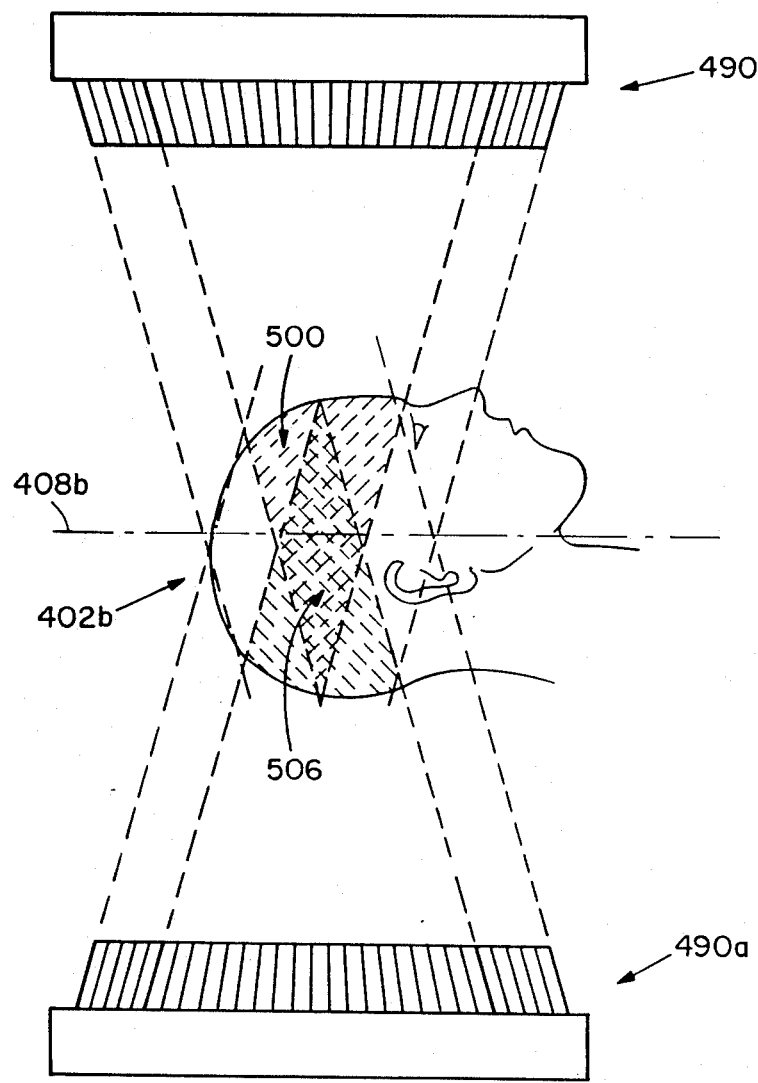
FIG. 24B is a schematic drawing of the collimator of FIG. 24A showing the difference in sensitivities among portions of the object as the collimator is rotated.

Collimator systems according to this invention also have focusing characteristics of the compound collimator in the dimension containing the axis of rotation. Collimator system 490, FIG. 24A, includes collimator elements 491 arranged in converging section 492 and parallel sections 494, 495. Section 492 has a section field of view 496 while parallel sections 494, 495 establish section field of view 498 through head 402b. Portion 500 is viewed with greater imaging sensitivity than portions 502, 504 viewed by sections 494, 495. A more detailed representation of the variation in imaging sensitivity is shown in FIG. 24B where collimator system 490 is shown rotated 180° about axis of rotation 408b as collimator system 490a. Within portion 500, three-dimensional rhombus 506 is provided with the greatest imaging sensitivity.

Figure 25:
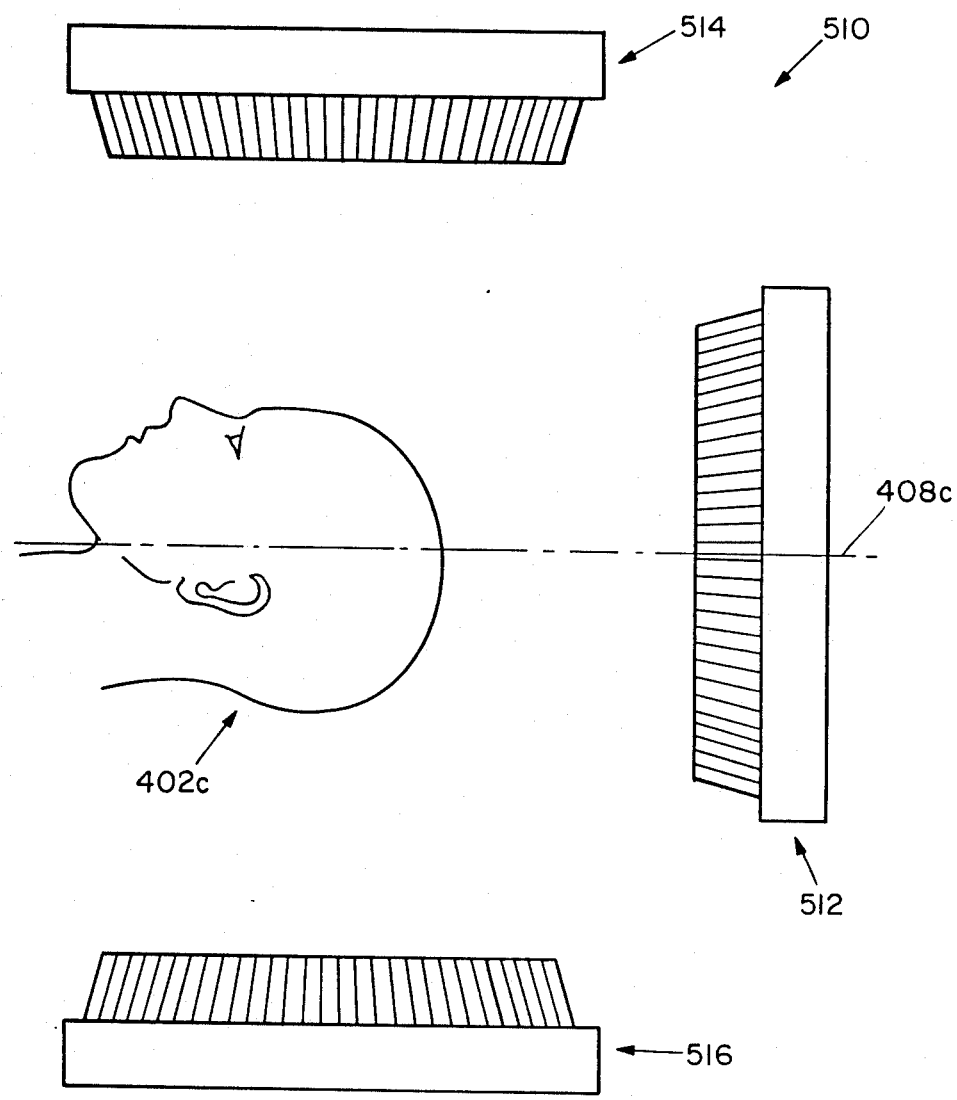
FIG. 25 is a schematic diagram of yet another collimator system according to this invention.

Enhanced imaging sensitivity can also be provided by providing an additional collimator segment whose collimator element axes form a different angle relative to lines parallel to the axis of rotation. Collimator system 510, FIG. 25, for example, has collimator segment 512 positioned with its collimator element axes at zero degrees, that is, parallel to axis of rotation 408c while segments 514, 516 are positioned with their collimator element axes disposed normal to axis of rotation 408c. Head 402c is thus imaged with an imaging sensitivity greater than that afforded solely by parallel type collimator segments 514, 516.

Although specific features of the invention are shown in some drawings and not others, this is for convenience only as each feature may be combined with any or al of the other features in accordance with the invention.

Other embodiments will occur to those skilled in the art and are within the following claims.

What is claimed is:

1. A collimator system rotatable about an axis of rotation for use in a radionuclide emission tomography camera for imaging a region of an object, comprising a collimator having a plurality of collimator elements for restricting and collimating radionuclide emissions within a field of view of said collimator, said collimator elements being disposed with their axes intersecting at least one line, parallel to the axis of rotation and within said collimator field of view, at at least two different angles, and said collimator elements comprising means for establishing a selected variation in imaging sensitivity across the imaging region.

2. The collimator system of claim 1 in which each collimator element axis is disposed at a different angle.

3. The collimator system of claim 1 in which said collimator element axes converge in at least one plane parallel to the axis of rotation.

4. The collimator system of claim 1 in which said collimator element axes diverge in at least one plane parallel to the axis of rotation.

5. A collimator system rotatable about an axis of rotation for use in a radionuclide emission tomography camera for imaging a region of an object, comprising a collimator having a plurality of collimator elements for restricting and collimating the radionuclide emissions within a field of view of said collimator, said collimator elements being disposed in at least two sets, at least one collimator element axis in one set intersecting a line, parallel to the axis of rotation and within said collimator field of view, at an angle different from that of at least one collimator element axis of the other set, and said collimator elements comprising means for providing at least two different imaging sensitivities across the imaging region.

6. The collimator system of claim 5 in which in at least one set the collimator element axes within that set have the same angle.

7. The collimator system of claim 5 in which in at least one set the collimator element axes within that set have angles which differ from each other.

8. The collimator system of claim 5 in which the collimator includes a collimator structure having each set of said collimator elements arranged in a different section, each section having a field of view proximate the field of view of the other section and establishing one of said different imaging sensitivities within its field of view.

9. The collimator system of claim 8 in which said section fields of view are non-overlapping.

10. The collimator system of claim 8 in which at least one of said sections is divided into two parts, one part being disposed on each side of said other section.

11. The collimator system of claim 8 in which said collimator elements are continuous throughout said collimator structure and are contiguous to each other.

12. The collimator system of claim 8 in which said section fields of view in combination encompass the entire object.

13. The collimator system of claim 8 in which at least one of said sections includes means for exhibiting uniform imaging sensitivity throughout said section.

14. The collimator system of claim 8 in which at least one of said sections includes means for exhibiting non-uniform imaging sensitivity throughout said section.

15. The collimator system of claim 8 in which at least one of said sections is selected from the group consisting of a parallel type collimator, a converging type collimator, and a diverging type collimator.

16. The collimator system of claim 8 in which said collimator structure is an annular rotatable collimator.

17. The collimator system of claim 8 in which said collimator structure is a planar collimator.

18. The collimator system of claim 5 in which each set of said collimator elements is a separate collimator segment, the fields of view of said segments establishing the different imaging sensitivities.

19. The collimator system of claim 18 in which said fields of view of said collimator segments overlap at least in part.

20. The collimator system of claim 19 in which said collimator segments include means for exhibiting imaging sensitivity in the portion of overlap.

21. The collimator system of claim 18 in which the field of view of one of the collimator segments completely overlaps that of the other said collimator segment.

22. The collimator system of claim 21 in which said other, overlapped collimator segment includes means for enhancing imaging sensitivity throughout its field of view.

23. The collimator system of claim 18 in which said collimator segments are segments of a planar collimator.

24. The collimator system of claim 18 in which said collimator segments are segments of an arcuate collimator.

25. The collimator system of claim 18 in which said segment fields of view in combination encompass the entire object.

26. The collimator system of claim 18 in which at least one of said collimator segments includes means for exhibiting uniform imaging sensitivity.

27. The collimator system of claim 18 in which at least one of said collimator segments includes means for exhibiting non-uniform imaging sensitivity.

28. The collimator system of claim 18 in which at least one of said collimator segments is selected from the group consisting of a parallel type collimator, a converging type collimator, and a diverging type collimator.

29. The collimator system of claim 18 in which said collimator segments are segments of an annular rotatable collimator.

30. The collimator system of claim 5 in which at least one of said sets of collimator elements has at least one collimator element axis substantially parallel to the axis of rotation.

31. A radionuclide emission tomography camera for imaging a region of an object, comprising:
a collimator having a plurality of collimator elements for restricting and collimating radionuclide emissions within a field of view of said collimator, said collimator elements being disposed with their axes intersecting at least one line, parallel to the axis of rotation and within said collimator field of view, at at least two different angles, and said collimator elements establishing a selected variation in imaging sensitivity across the imaging region;
means, responsive to said collimator, for detecting radionuclide emissions from the region to collect at least one collimated image through each collimator element; and
means for combining the collimated images to produce a final image of the imaging region exhibiting said selected variation in imaging sensitivity across the imaging region.

* * * * *

UNITED STATES PATENT OFFICE
CERTIFICATE OF CORRECTION

PATENT NO. : 4,859,852
DATED : August 22, 1989
INVENTOR(S) : Sebastian Genna, Andrew P. Smith It is certified that error appears in the above-identified patent and that said Letters Patent is hereby corrected as shown below:

Column 1, line 1, the following should be inserted:

-- This invention was made with Government support under Department of Health and Human Services Grant No. NS24609-03 awarded by the National Institute of Neurological and Communicative Disorders and Stroke. The Government has certain rights in the invention. --

Signed and Sealed this

Twenty-fourth Day of November, 1992

Attest:

DOUGLAS B. COMER

*Attesting Officer*  *Acting Commissioner of Patents and Trademarks*